(12) United States Patent
Srinivasan et al.

(10) Patent No.: US 10,729,858 B2
(45) Date of Patent: Aug. 4, 2020

(54) NEEDLE STORAGE MAGAZINE WITH STATUS INDICATION

(71) Applicant: Becton, Dickinson and Company, Franklin Lakes, NJ (US)

(72) Inventors: Sudarsan Srinivasan, North Brunswick, NJ (US); David Schiff, Highland Park, NJ (US); Stephan Lawson, Malvern, PA (US); Nicholas Hugh McGill, Broomall, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/095,539

(22) PCT Filed: Mar. 31, 2017

(86) PCT No.: PCT/US2017/025311
§ 371 (c)(1),
(2) Date: Oct. 22, 2018

(87) PCT Pub. No.: WO2017/189167
PCT Pub. Date: Nov. 2, 2017

(65) Prior Publication Data
US 2019/0083718 A1    Mar. 21, 2019

Related U.S. Application Data

(60) Provisional application No. 62/328,649, filed on Apr. 28, 2016.

(51) Int. Cl.
*A61M 5/00* (2006.01)
*A61M 5/50* (2006.01)
(Continued)

(52) U.S. Cl.
CPC ............ *A61M 5/5086* (2013.01); *A61M 5/00* (2013.01); *A61M 5/002* (2013.01);
(Continued)

(58) Field of Classification Search
CPC ........................ A61M 2005/004; A61M 5/002
See application file for complete search history.

(56) References Cited

U.S. PATENT DOCUMENTS 5,829,589 A    11/1998   Nguyen et al.
5,873,462 A     2/1999   Nguyen et al.
(Continued)

FOREIGN PATENT DOCUMENTS

EP    2119423 A1    11/2009
EP    2420270 A2     2/2012
(Continued)

OTHER PUBLICATIONS

Li-Yuan Chang et al., "Integrated Flow Sensing for Focal Biochemical Stimulation", Proceedings of the Third IEEE International Conference on Nano/Micro Engineered and Molecular Systems, Jan. 6-9, 2008, Sanya, China, pp. 921-926, (6 Pages Total).

*Primary Examiner* — Gene O Crawford
*Assistant Examiner* — Ayodeji T Ojofeitimi
(74) *Attorney, Agent, or Firm* — Dickinson Wright PLLC

(57) ABSTRACT

A magazine (18) that stores a plurality of needles (56) configured to engage a medication pen (2) for medication delivery, the magazine (18) comprising a magazine housing (20) enclosing a removable array (26) having a plurality of hub chambers (22) each enclosing one of a plurality of needle hubs (50), a connector (28) in each of the plurality of hub chambers (22), each connector (28) engages one of the plurality of needle hubs (50), a plurality of peel tabs (30) each sealing one of the plurality of hub chambers (22), and an electronic indicator (62) to identify a status of the
(Continued)

plurality of needle hubs (50), wherein the electronic indicator (62) identifies how many of the plurality of needle hubs (50) are unused.

21 Claims, 21 Drawing Sheets

(51) Int. Cl.
  *A61M 5/34* (2006.01)
  *A61M 5/32* (2006.01)
  *A61M 5/24* (2006.01)
(52) U.S. Cl.
  CPC ........ *A61M 5/3293* (2013.01); *A61M 5/3297* (2013.01); *A61M 5/345* (2013.01); *A61M 5/3205* (2013.01); *A61M 2005/004* (2013.01); *A61M 2005/2474* (2013.01); *A61M 2205/3306* (2013.01); *A61M 2205/3313* (2013.01); *A61M 2205/3327* (2013.01); *A61M 2205/3584* (2013.01); *A61M 2205/502* (2013.01); *A61M 2205/52* (2013.01); *A61M 2205/583* (2013.01); *A61M 2205/584* (2013.01); *A61M 2205/587* (2013.01); *A61M 2205/8206* (2013.01)

(56) References Cited

U.S. PATENT DOCUMENTS

| | | | |
|---|---|---|---|
| 5,931,817 A | 8/1999 | Nguyen et al. | |
| 6,202,642 B1* | 3/2001 | McKinnon | A61M 15/009 128/200.14 |
| 6,536,944 B1* | 3/2003 | Archibald | B01J 19/0046 219/497 |
| 8,876,780 B2 | 11/2014 | Bruehwiler et al. | |
| 9,101,724 B2 | 8/2015 | Chapin et al. | |
| 9,107,988 B2 | 8/2015 | Bruehwiler et al. | |
| 9,155,838 B2 | 10/2015 | Bilton et al. | |
| 9,381,303 B2 | 7/2016 | Abhijitsinh et al. | |
| 9,717,860 B2 | 8/2017 | Bruehwiler et al. | |
| 10,029,042 B2 | 7/2018 | Searle et al. | |
| 2001/0014792 A1 | 8/2001 | West et al. | |
| 2002/0020646 A1 | 2/2002 | Groth et al. | |
| 2002/0020647 A1 | 2/2002 | Groth | |
| 2005/0084631 A1 | 4/2005 | Anderson | |
| 2008/0312604 A1 | 12/2008 | Boesen | |
| 2010/0217206 A1 | 8/2010 | Lum et al. | |
| 2011/0068034 A1 | 3/2011 | Hwang et al. | |
| 2012/0004620 A1 | 1/2012 | Spool et al. | |
| 2012/0016315 A1 | 1/2012 | Radmer et al. | |
| 2012/0041373 A1 | 2/2012 | Bruehwiler et al. | |
| 2012/0041381 A1 | 2/2012 | Raj et al. | |
| 2012/0041383 A1 | 2/2012 | Bruehwiler et al. | |
| 2012/0041390 A1* | 2/2012 | Spool | A61M 5/002 604/240 |
| 2013/0041321 A1 | 2/2013 | Cross et al. | |
| 2013/0053751 A1 | 2/2013 | Holtham | |
| 2013/0341849 A1* | 12/2013 | Shimazaki | A61M 5/002 269/287 |
| 2014/0027329 A1* | 1/2014 | Dasbach | A61M 5/002 206/366 |
| 2014/0076758 A1 | 3/2014 | Dasbach et al. | |
| 2014/0123479 A1 | 5/2014 | Dasbach | |
| 2014/0262884 A1 | 9/2014 | Priebe et al. | |
| 2014/0299622 A1 | 10/2014 | Hofmann et al. | |
| 2014/0303570 A1* | 10/2014 | Hofmann | A61M 5/3205 604/272 |
| 2014/0339113 A1 | 11/2014 | Hofmann et al. | |
| 2015/0025469 A1 | 1/2015 | Larsen et al. | |
| 2015/0048100 A1* | 2/2015 | Dickie | A61J 7/0481 221/1 |
| 2015/0163898 A1 | 6/2015 | Mokhtarzad | |
| 2015/0335827 A1 | 11/2015 | Stefansen et al. | |
| 2015/0346184 A1 | 12/2015 | Galasso | |
| 2016/0000992 A1 | 1/2016 | Steel et al. | |
| 2016/0030683 A1 | 2/2016 | Taylor et al. | |
| 2016/0074587 A1 | 3/2016 | Searle et al. | |
| 2016/0082195 A1 | 3/2016 | Atterbury et al. | |
| 2016/0106925 A1 | 4/2016 | Boesen | |
| 2018/0361056 A1* | 12/2018 | Horlock | A61M 5/002 |

FOREIGN PATENT DOCUMENTS

| | | |
|---|---|---|
| EP | 2517743 A1 | 10/2012 |
| EP | 2586475 A1 | 5/2013 |
| EP | 2696913 B1 | 9/2015 |
| WO | 2008/150715 A1 | 12/2008 |
| WO | 2014/020001 A1 | 2/2014 |
| WO | 2016/050902 A1 | 4/2016 |

\* cited by examiner

NEEDLE STORAGE MAGAZINE WITH STATUS INDICATION

This application claims the benefit under 35 U.S.C. § 119(e) of U.S. Provisional Patent Application Ser. 62/328, 649, filed on Apr. 28, 2016, which is hereby incorporated by reference in its entirety.

FIELD

Various exemplary embodiments of the invention relate to needle storage for medication pens.

BACKGROUND

Medication pens are typically used to inject medication into a patient. A person who must periodically self-inject doses of medication will typically carry a medication pen and several single-use pen needles. A medication pen is designed for safety and sterility. However, inefficiencies and inconveniences arise.

SUMMARY OF THE INVENTION

It is an aspect of the present invention to provide a magazine that stores a plurality of needles configured to engage a medication pen for medication delivery. Such a magazine provides advantages in minimizing the size of pen needle packaging, minimizing the volume of plastic used to manufacture components and grouping together a number of pen needles making them easy to use and carry. Moreover, the magazine includes an electronic indicator that advantageously provides a user at least one of a battery level, needle hub use status, current conditions and a number of unused needle hubs.

Having a magazine of needles available for medication delivery reduces needle reuse. Needle reuse is undesired for at least the following reasons. The needle dulls after a single use and so subsequent use may cause pain to the patient. Multiple needle use can also reduce the strength of the needle tip which may cause a potential fracture. Also, needle reuse increases sanitary concerns and health risks to the patient.

The needle assembly of the present invention advantageously reduces reuse for at least the following reasons. Although patients may desire to financially benefit from using a needle multiple times, the needle assembly is configured to prevent each of the plurality of needles from being used more than once. Convenience is another reason patients reuse needles. Patients may also be concerned about not having another needle available for use or not having access to supplies. However, the needle assembly conveniently provides multiple needles so that an unused needle is more readily available.

The foregoing and/or other aspects of the present invention can be achieved by providing a magazine that stores a plurality of needles configured to engage a medication pen for medication delivery, the magazine comprising a magazine housing enclosing a removable array having a plurality of hub chambers each enclosing one of a plurality of needle hubs, a connector in each of the plurality of hub chambers, each connector engaging one of the plurality of needle hubs, a plurality of closures each sealing one of the plurality of hub chambers, and an electronic indicator to identify a status of the plurality of needle hubs, wherein the electronic indicator identifies how many of the plurality of needle hubs are unused.

Preferably, the magazine housing includes mounting recesses, the removable array includes mounting projections, and the mounting projections engage the mounting recesses to secure the removable array to the magazine housing. The removable array is replaced when the plurality of needle hubs in the removable array are all used and the removable array includes two removable arrays which are disposed opposite each other.

Preferably, the electronic indicator includes a plurality of LEDs, wherein each of the plurality of LEDs is aligned to one of the plurality of hub chambers. When one of the plurality of LEDs corresponding to one of the plurality of hub chambers illuminates in a selected color, the corresponding needle hub of the plurality of needle hubs is used. When one of the plurality of LEDs corresponding to one of the plurality of hub chambers illuminates in another selected color, the corresponding needle hub of the plurality of needle hubs is new and available for use.

Preferably, the magazine housing includes a circuit board including an inertial measurement unit that detects vibration, the inertial measurement unit triggering operation of the circuit board when a predetermined vibration value is exceeded.

Preferably, the electronic indicator includes an infrared reflective system that emits infrared light to determine the status of the plurality of needle hubs. The infrared reflective system includes a plurality of infrared emitters and a plurality of infrared detectors. One of the plurality of infrared emitters and one of a plurality of infrared detectors are aligned to each other in each one of the plurality of hub chambers. Based on infrared light reflection received, the infrared reflective system identifies one of an empty hub chamber, an unused needle hub in the hub chamber and a used needle hub in the hub chamber. The magazine housing is preferably an infrared translucent material and the plurality of needle hubs is preferably an infrared reflective material.

Preferably, the electronic indicator includes an electronic display. The electronic display includes at least one of a battery level, use status, current conditions and a number of the unused needle hubs. The current conditions display the current date and time and the use status displays a time when a most recent needle hub of the plurality of needle hubs was removed from the magazine housing.

The foregoing and/or other aspects of the present invention can also be achieved by a method of using a plurality of needles in a magazine, the plurality of needles is configured to engage a medication pen for medication delivery, the method comprising removing a selected closure of a plurality of closures to expose a selected needle hub of a plurality of needle hubs in a magazine housing, engaging the medication pen to the selected needle hub, disengaging the selected needle hub from the magazine housing to prepare the medication pen for medication delivery, and indicating a status of the plurality of needles by identifying how many of the plurality of needle hubs are unused.

It will be understood that each of the preferred or optional features of the various embodiments described above may be combined with other preferred or optional features. Additionally, features described in combination with one particular embodiment may also be combined with one of the other embodiments.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which.

DETAILED DESCRIPTION OF EXEMPLARY EMBODIMENTS

Figure 1:
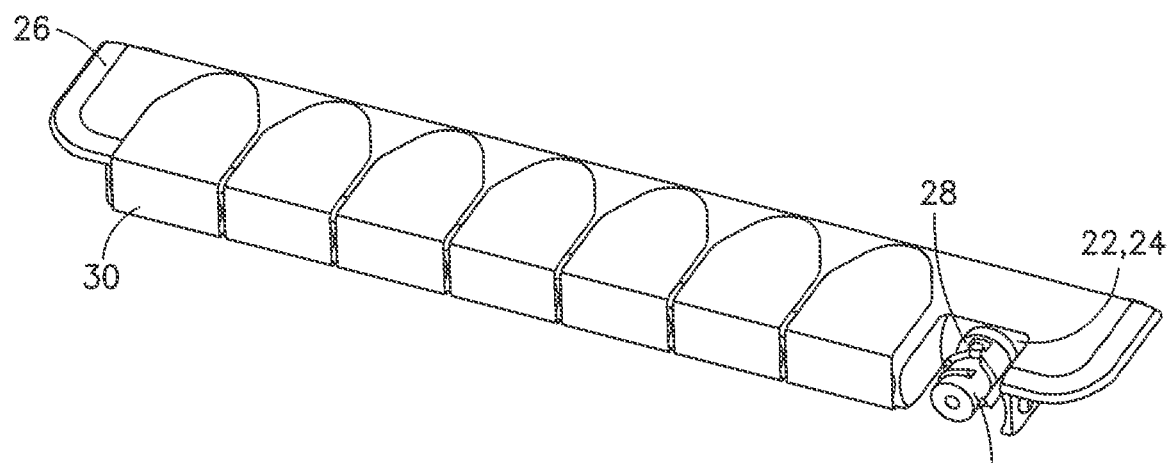
FIG. 1 illustrates a left perspective view of a removable magazine array.

According to one embodiment, FIGS. 1-4 illustrate a magazine 18 that stores a plurality of needles or cannulas used by a medication pen 2 for medication delivery. The magazine 18 includes a magazine housing 20, a plurality of hub chambers 22 each including a connector 28, a selected hub chamber 24, and magazine arrays 26. The magazine housing 20 is in the shape of a credit card and encloses each of the plurality of needles or cannulas.

Figure 3:
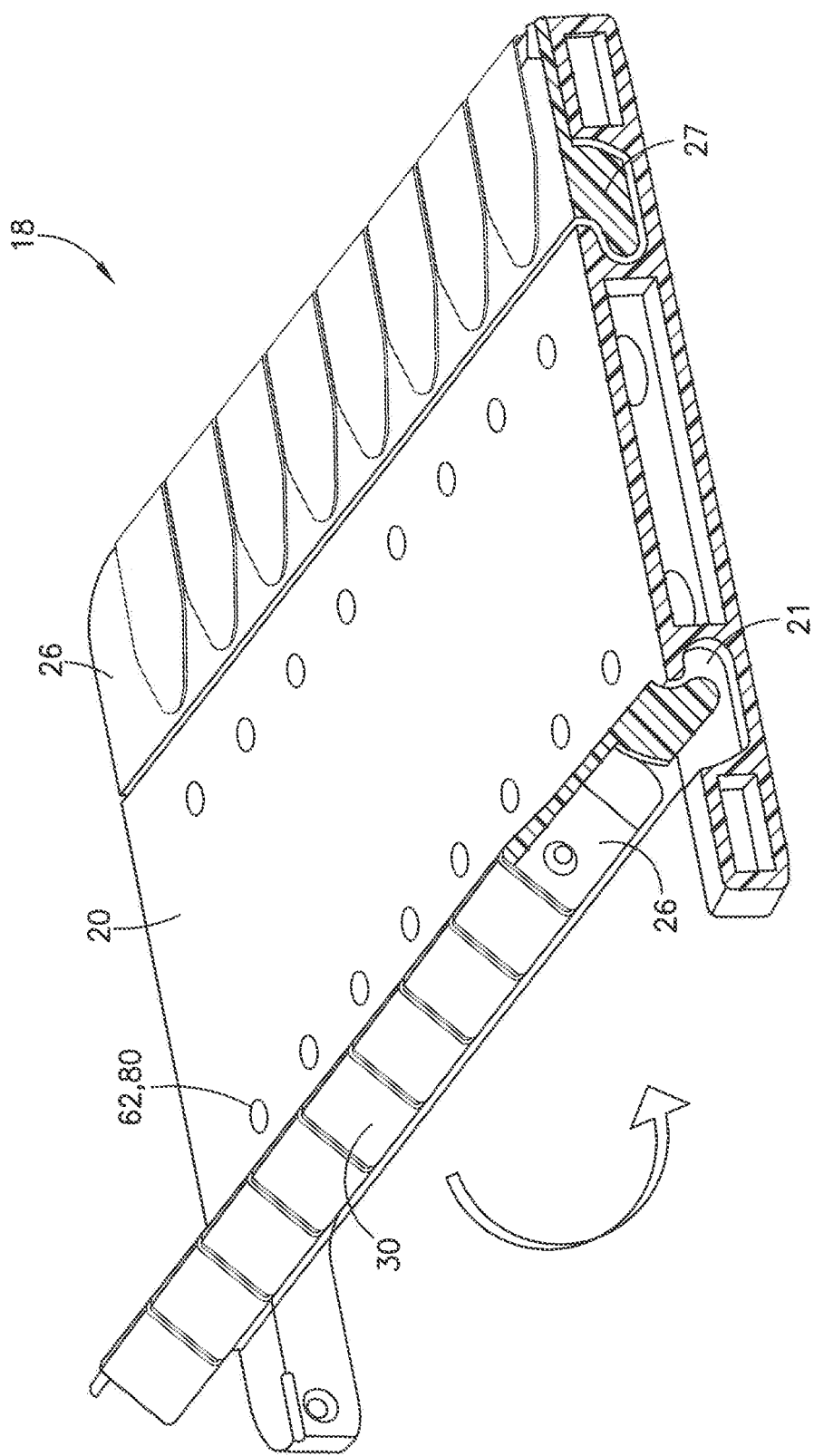
FIG. 3 illustrates a left perspective view of the removable magazine arrays disposed in the magazine housing.
Figure 4:
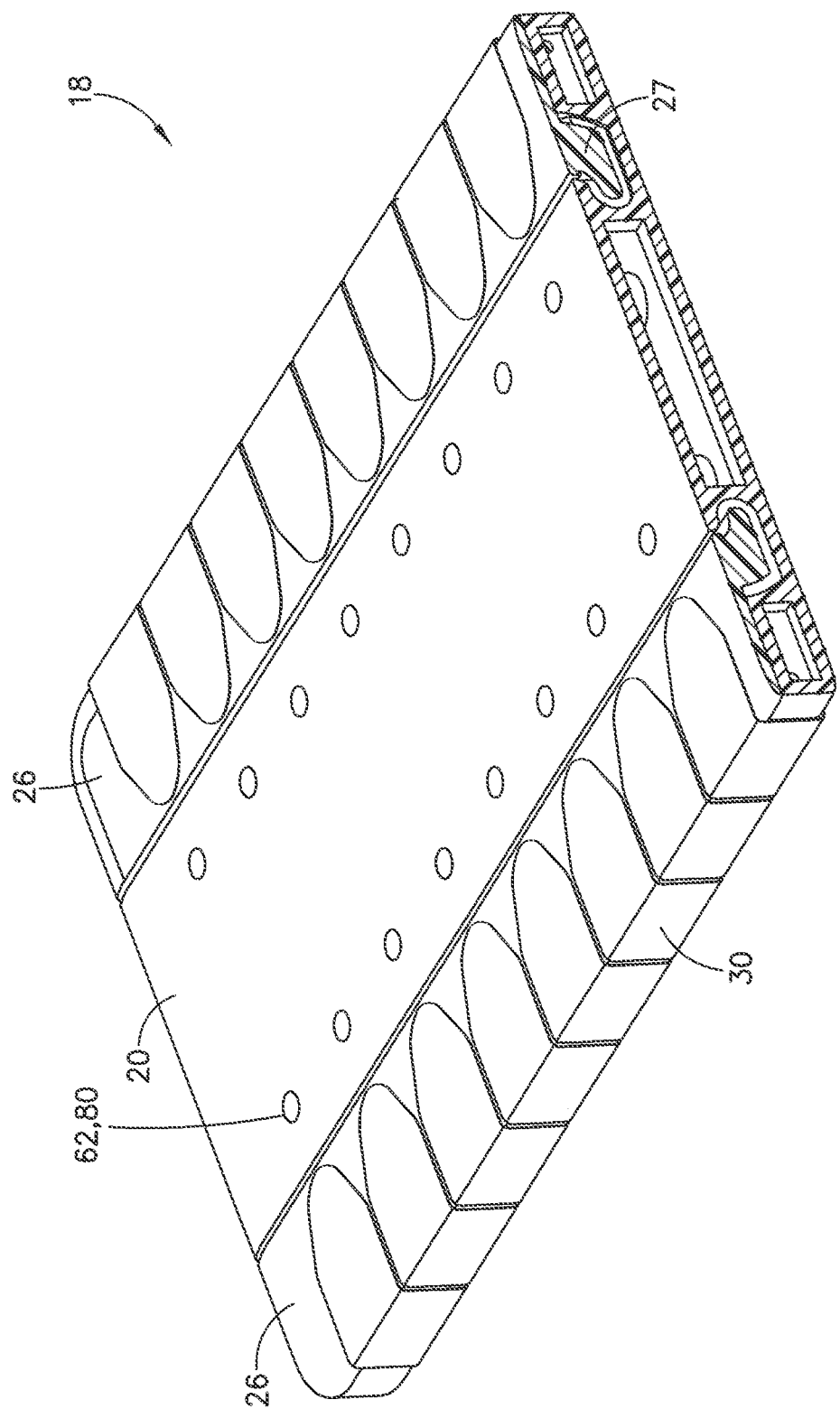
FIG. 4 illustrates a left perspective view of an exemplary magazine.

As illustrated in FIG. 1, the magazine housing 20 includes two magazine arrays 26. Each of the magazine arrays 26 carries one of a plurality of needle hubs 50 in each of the plurality of hub chambers 22. Preferably, each magazine array 26 includes eight hub chambers 22 although more or less is contemplated. As illustrated in FIGS. 3 and 4, the magazine arrays 26 are opposite one another in a longitudinal direction. The plurality of needle hubs 50 are inline and adjacent to one another.

The magazine arrays 26 are also removable. Specifically, when all of the plurality of needle hubs 50 in the magazine array 26 are used, the magazine array 26 can be discarded and replaced. Accordingly, the magazine housing 20 is reusable. This is advantageous because the magazine housing 20 contains electronics and is, therefore, more expensive.

Such a configuration advantageously provides a small, compact and optimized arrangement of the plurality of needle hubs 50 and allows the magazine 18 to be made from a minimal amount of material. Additionally, each of the plurality of needle hubs 50 is individually disposed in each of the plurality of hub chambers 22 to advantageously provide a separate cavity for each needle hub 50.

Each of the plurality of hub chambers 22 includes the connector 28 which secures each of the plurality of needle hubs 50. The connector 28 is preferably a quarter turn bayonet connection, although a push-pull detent connector can also be used. Further details of the connector 28 are described below.

Each of the plurality of hub chambers 22 is enclosed by a peel tab or closures 30. The plurality of peel tabs 30 is preferably a foil tab. The peel tabs 30 is preferably composed of, or coated with, an infrared reflective material. The peel tab 30 individually seals and provides a sterile environment for each of the plurality of needle hubs 50 disposed in the plurality of hub chambers 22. Such a configuration advantageously provides independent access to each of the plurality of needle hubs 50. As a result, one of the plurality of needle hubs 50 is used without altering the sterile environment of the remaining needle hubs 50.

FIG. 1 also illustrates one of the plurality of peel tabs 30 removed to expose a selected hub chamber 24 of the plurality of hub chambers 22. The selected hub chamber 24 includes a selected needle hub 52 ready for use.

Figure 2:
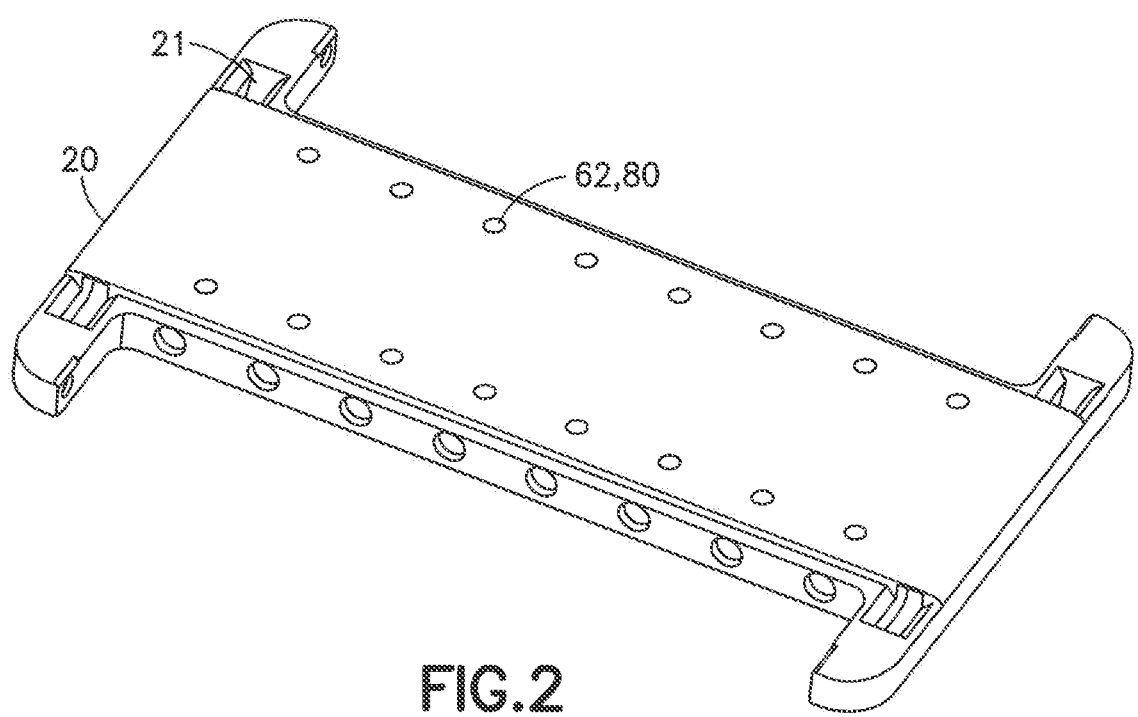
FIG. 2 illustrates a left perspective view of a magazine housing.

FIG. 2 illustrates the magazine housing 20 with the magazine arrays 26 removed. The magazine housing 20 is preferably made of an infrared translucent material and includes an electronic indicator 62. According to one embodiment, the electronic indicator 62 is a plurality of LEDs 80. The plurality of LEDs 80 indicates a status of the plurality of needle hubs 50. Each of the plurality of LEDs 80 is positioned to a corresponding one of the plurality of hub chambers 22.

Figure 18:
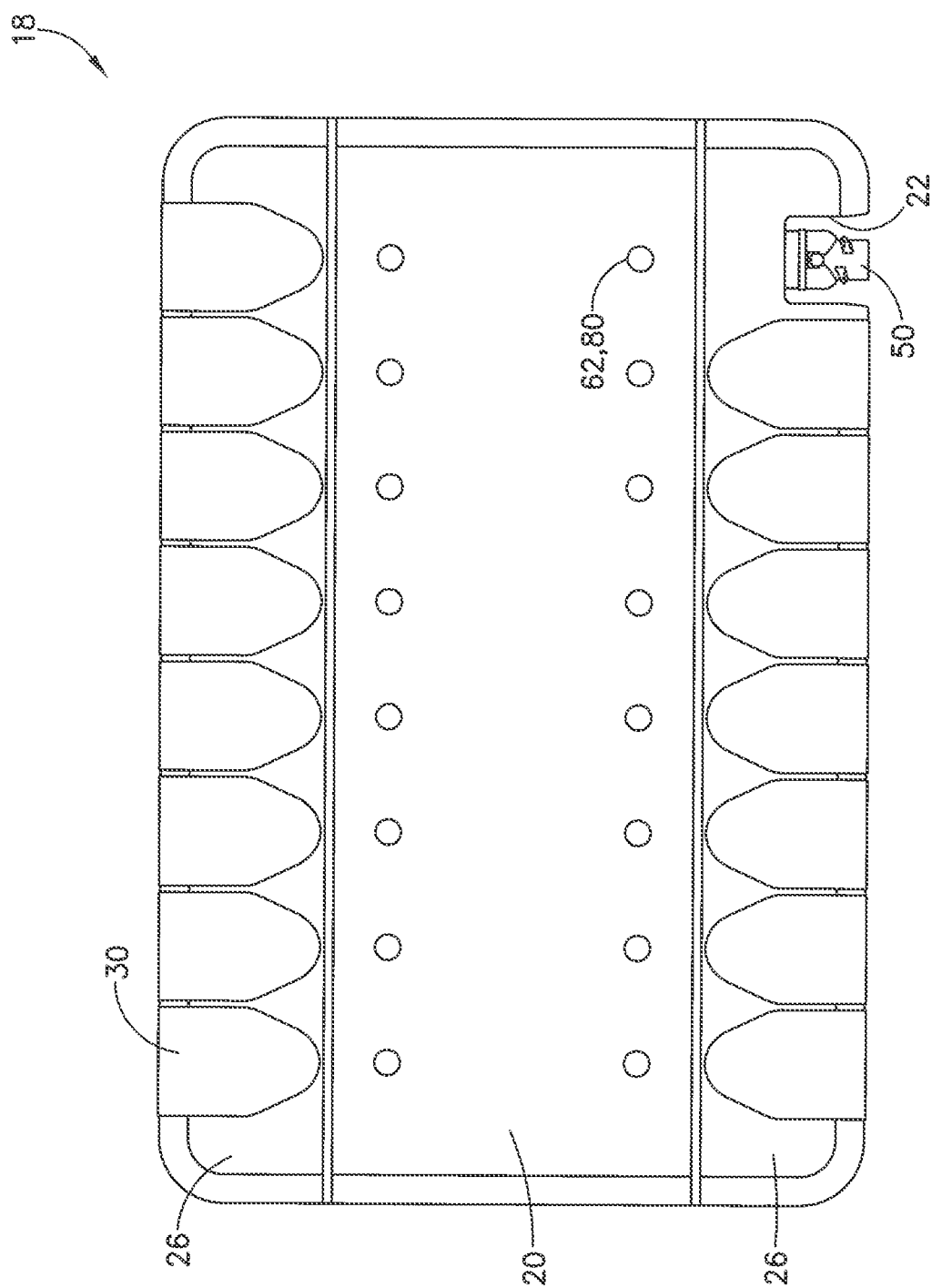
FIG. 18 illustrates the magazine including electronic indicators being LEDs to identify a status of the plurality of needle hubs.

As illustrated in FIG. 18, the LEDs 80 illuminate a color to indicate the status of the plurality of needles hubs 50. For example, if the LED 80 illuminates as green, the corresponding needle hub 50 of the plurality of needle hubs 50 is new (unused) and available for use. If the LED 80 illuminates as red, the corresponding needle hub 50 of the plurality of needle hubs 50 is used and should not be reused. If the LED 80 illuminates as orange, the corresponding hub chamber 22 of the plurality climb chambers 22 is empty and not occupied by one of the plurality of needle hubs 50. In other words, the selected needle hub 52 is removed from the magazine housing 20 for use. The plurality of LEDs 80 cooperates with an infrared reflective system 68, as further described below, to determine the device status of each of the plurality of needle hubs 50.

The magazine housing 20 also includes mounting recesses 21 that engage and secure each of the magazine arrays 26. FIG. 3 illustrates that the mounting recesses 21 are disposed on each side of the magazine housing 20. The mounting recesses 21 are paired for each magazine array 26. FIG. 3 also illustrates mounting projections 27 on each side of the magazine array 26 beginning to engage the magazine housing 20. The mounting projections 27 of the other magazine array 26 fully engage the mounting recesses 21 of the magazine housing 20 to secure the magazine arrays 26 in the magazine housing 20. FIG. 4 illustrates the both magazine arrays 26 secured in the magazine housing 20.

This interface between the magazine arrays 26 and the magazine housing 20 advantageously allows the magazine arrays 26 to be replaced when all the needle hubs 50 are used. The magazine arrays 26 being secured to and removed from the magazine housing 20 advantageously prevent the magazine housing 20 from being discarded after all the needle hubs 50 are used. Instead, the magazine housing 20 is reused with new magazine arrays 26.

Figure 5:
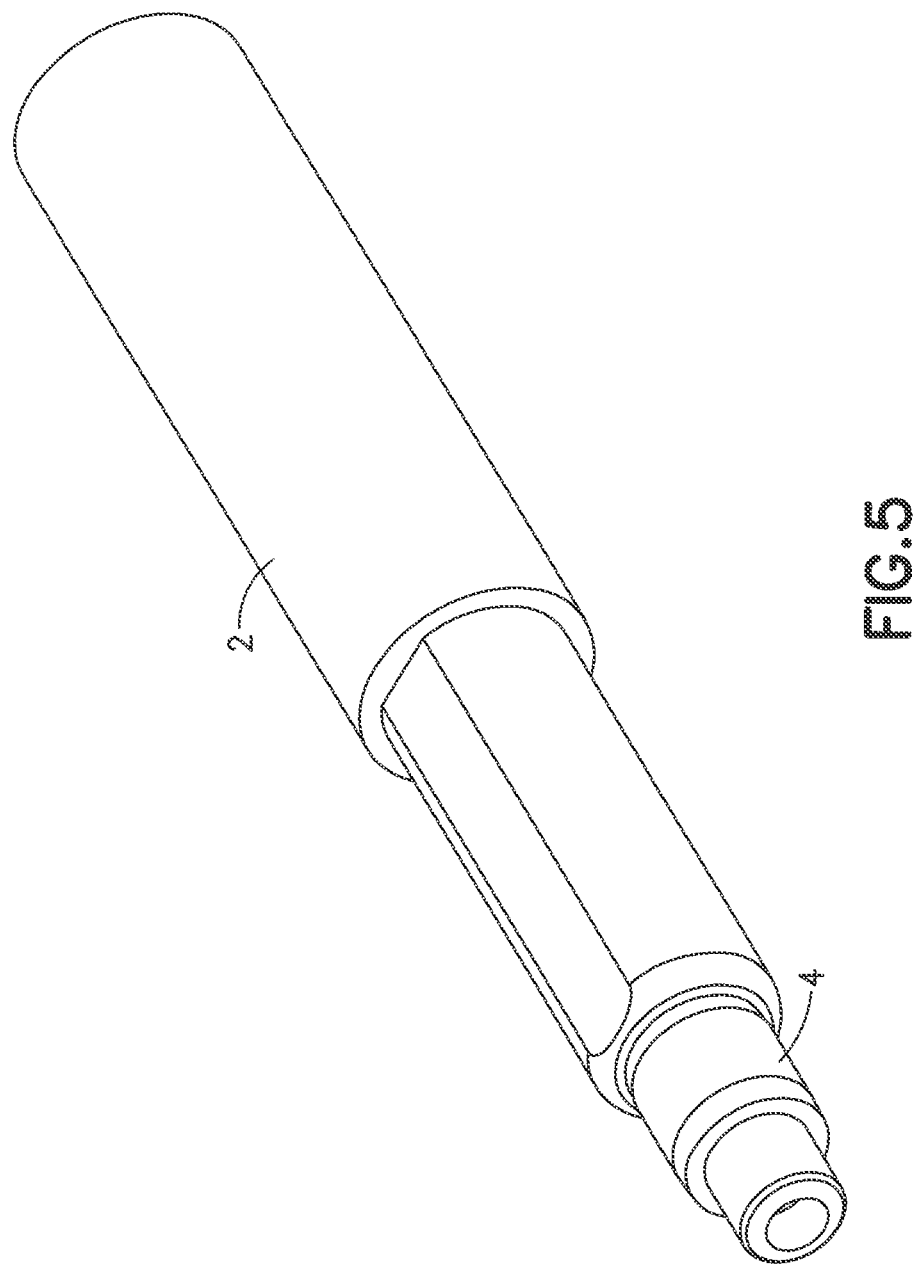
FIG. 5 illustrates a right perspective view of an exemplary adapter connected to a medication pen.
Figure 6:
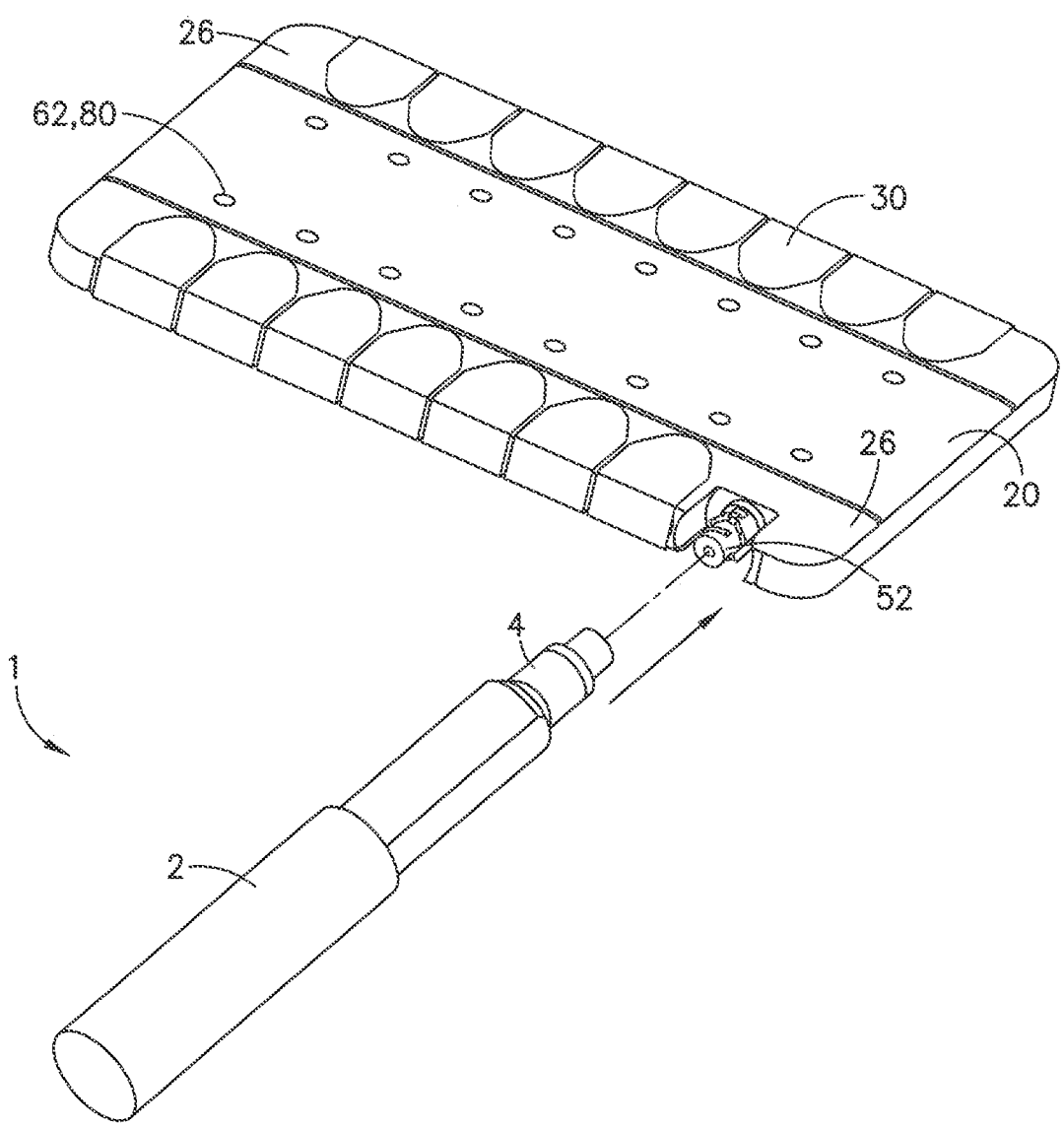
FIG. 6 illustrates a right perspective view of the medication pen prior to engaging a needle hub in the magazine housing.
Figure 7:
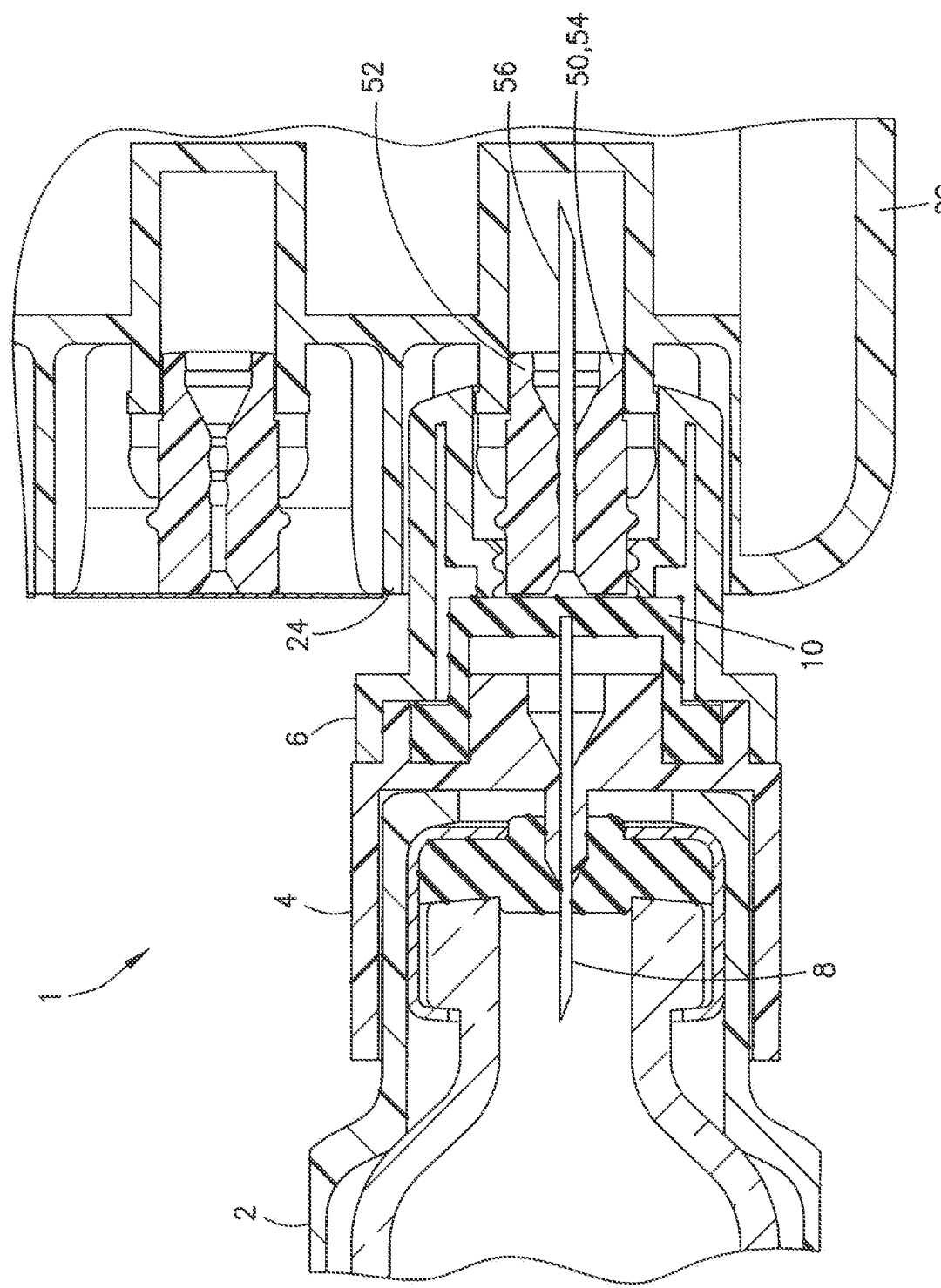
FIG. 7 illustrates a partial cross sectional view of the medication pen of FIG. 5 beginning to engage a needle hub in a magazine housing.
Figure 9:
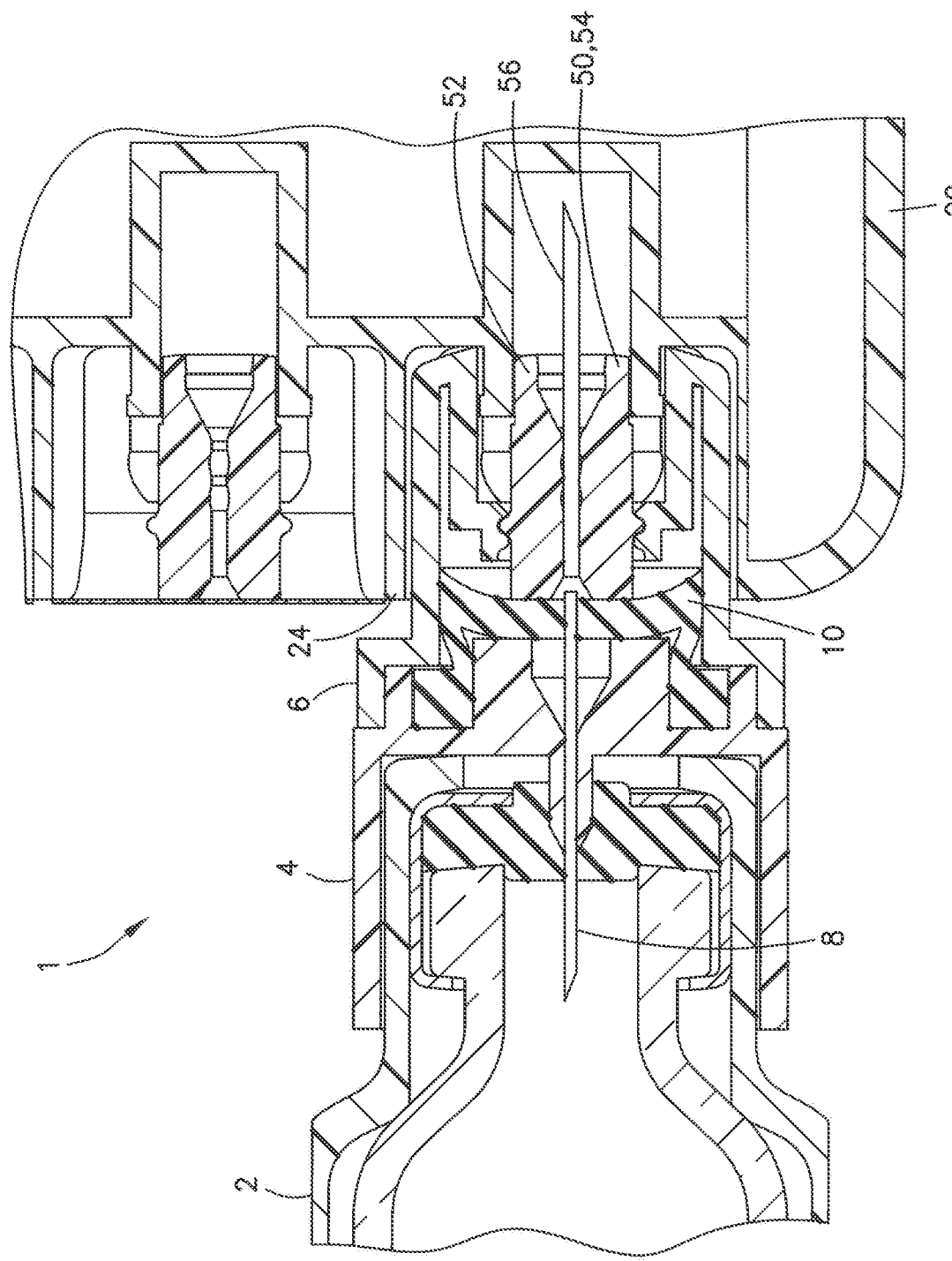
FIG. 9 illustrates a partial cross sectional view of the medication pen of FIG. 5 fully engaged to the needle hub in the magazine housing.

FIG. 5, according to one embodiment, illustrates a medication pen 2 connected to an adapter 4. The adapter 4 is attachable to a standard reusable medication pen 2 (i.e. pen injector). The components of the adapter 4 are illustrated in FIGS. 7 and 9. FIG. 6 illustrates the adapter 4 connected to the medication pen 2 and beginning to engage the selected needle hub 52.

As illustrated in FIG. 7, the adapter 4 includes an adaptor body 6, an adapter cannula 8 and an adapter septum 10. The adapter body 6 is preferably a two piece press-fit assembly that encloses and secures the adapter septum 10. A proximal end of the adapter body 6 includes threads that are configured to engage threads in the medication pen 2. A distal end of the adapter body 6 includes an opening. The opening is configured to engage one of a plurality of needle hubs 50.

Preferably, the adapter septum 10 includes a preformed opening for the adapter cannula 8 to pierce. Alternately, a sharpened distal end of the adapter cannula 8 pierces the adapter septum 10 to establish fluid communication. The adapter septum 10 is preferably made of silicon rubber.

The adapter cannula 8 is fixed to the adapter body 6. The adapter cannula 8 is disposed in the proximal end of the adapter body 6 and is configured to pierce a septum (not shown) of the medication pen 2 to establish fluid communication with the medication pen 2. A distal end of the adapter cannula 8 is disposed in the adapter septum 10. Operation of the adapter cannula 8 with the adapter septum 10 is described below.

The adapter septum 10 regulates the flow of medicament between the medication pen 2 and the selected needle hub 52. The adapter septum 10 is closed in its natural state. As illustrated in FIG. 7, the adapter septum 10 partially engages the adapter cannula 8 at its distal end in the closed position. Since the selected needle hub 52 in not fully engaged with the adapter 4, the adapter septum 10 remains in the closed position. That is, the adapter septum 10 of FIG. 7 is in its natural state.

FIG. 9 illustrates the adapter septum 10 in an open position. The selected needle hub 52 is fixed to the adapter body 6 via a push-pull detest although other methods are contemplated. When the selected needle hub 52 is fixed to the adapter body 6, the selected needle hub 52 applies an axial force to the adapter septum 10. The axial force causes the adapter septum 10 to flex (or compress) and allows the adapter cannula 8 to pierce the adapter septum 10 and extend into the selected needle hub 52. The axial force also establishes a sealing surface to prevent a leak path at an interface between a proximal end of the selected needle hub 52 and a distal surface of the adapter septum 10. Accordingly, the selected needle hub 52 is now in fluid communication with the medication pen 2.

Figure 8:
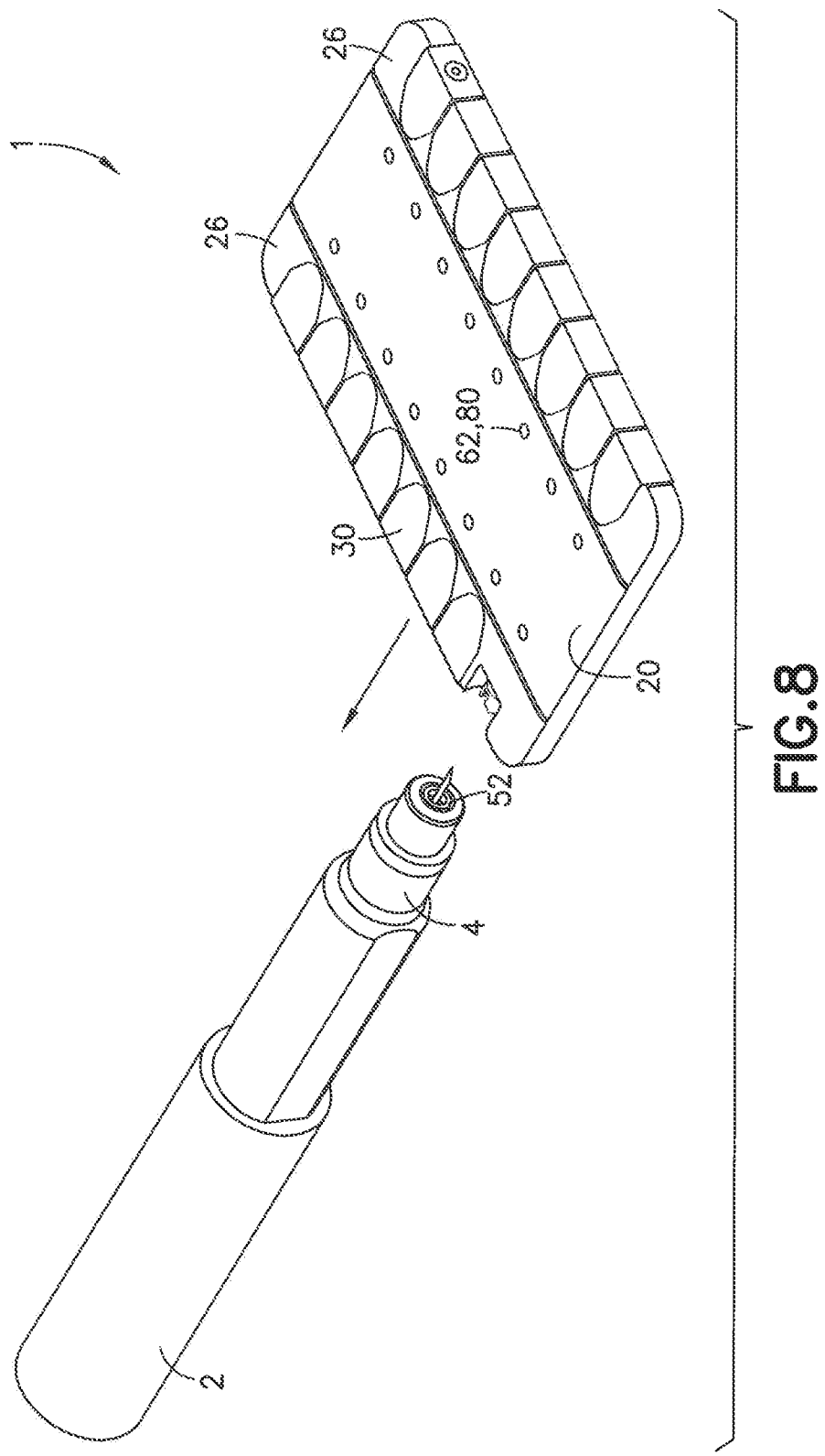
FIG. 8 illustrates a left perspective view of the magazine assembly where the medication pen engaged to the needle hub is being removed from the magazine housing.

According to one embodiment, FIG. 8 illustrates the magazine assembly 1 where the selected needle hub 52 is connected to the medication pen 2 via the adapter 4 (see also FIG. 9) and is removed from the magazine 18. Specifically, the selected needle hub 52 disengages the connector 28 in the selected hub chamber 24 of the magazine housing 20. Each of the plurality of needle hubs 50 cannot be easily removed from the magazine housing 20 without using the adapter 4. The medication pen 2 is now ready for medication delivery.

Figure 10:
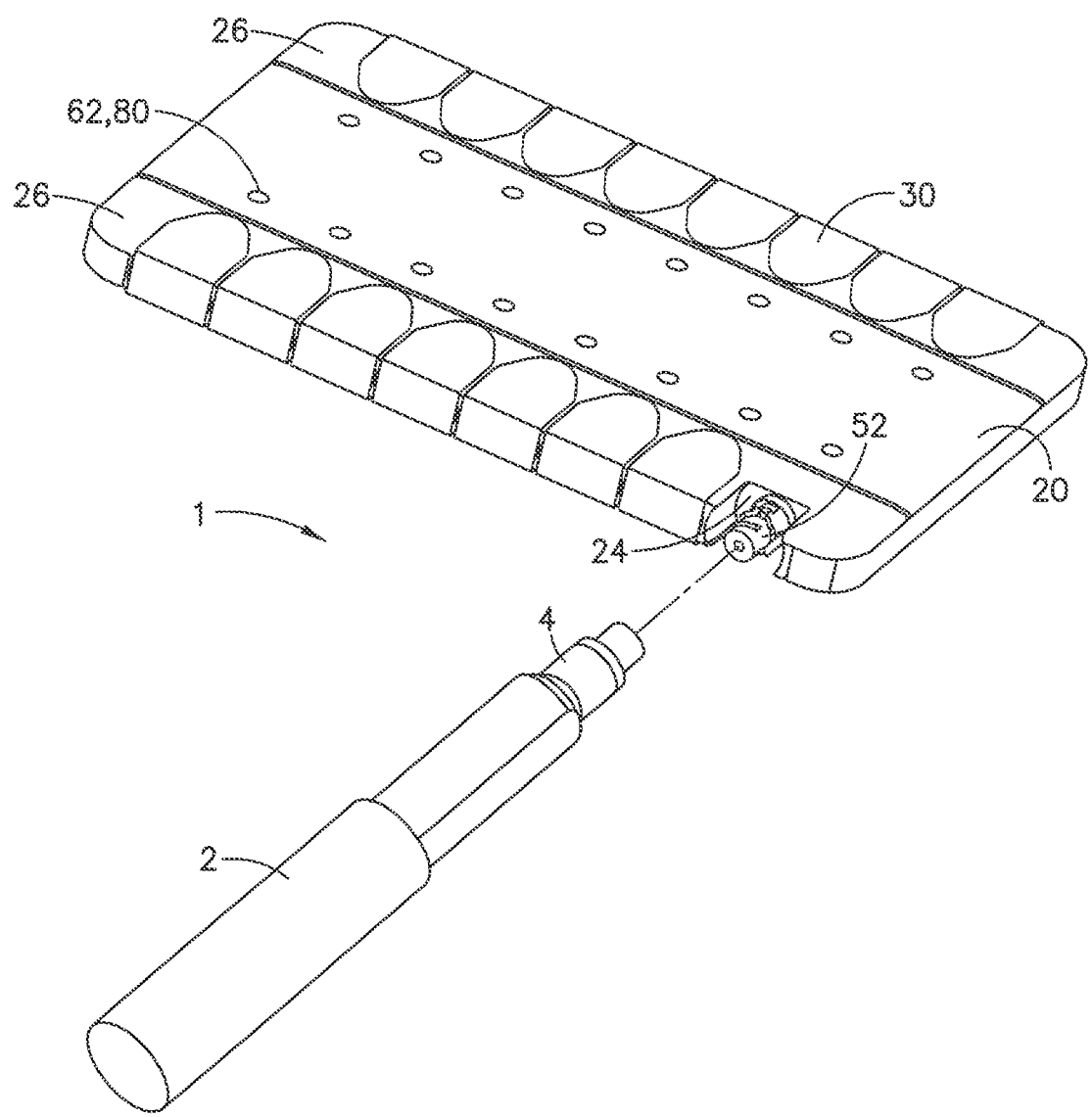
FIG. 10 illustrates a right perspective view of the magazine assembly where the medication pen returns the needle hub to the magazine housing.
Figure 11:
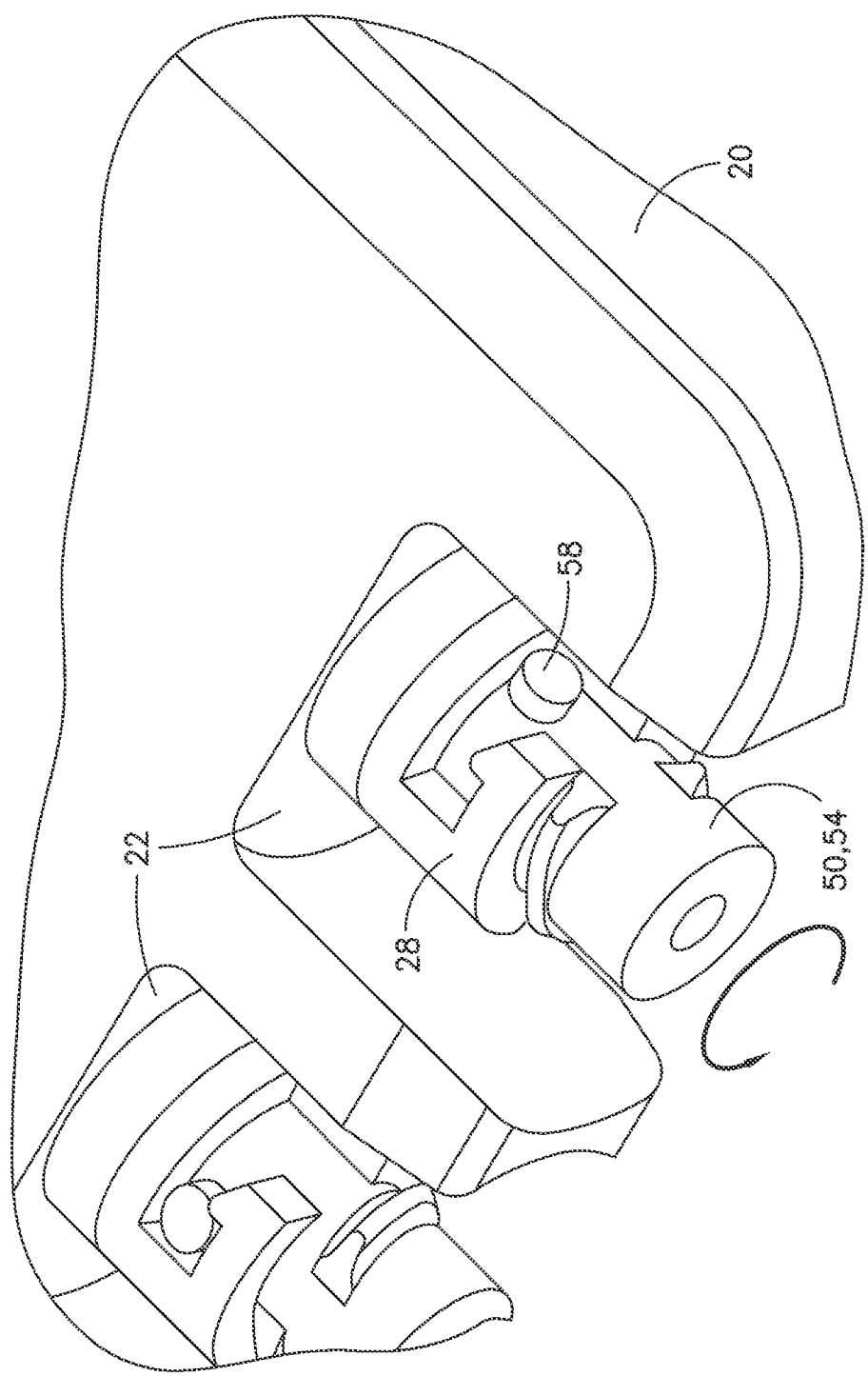
FIG. 11 illustrates a right perspective view of the needle hub in the magazine housing in an unlocked position.
Figure 12:
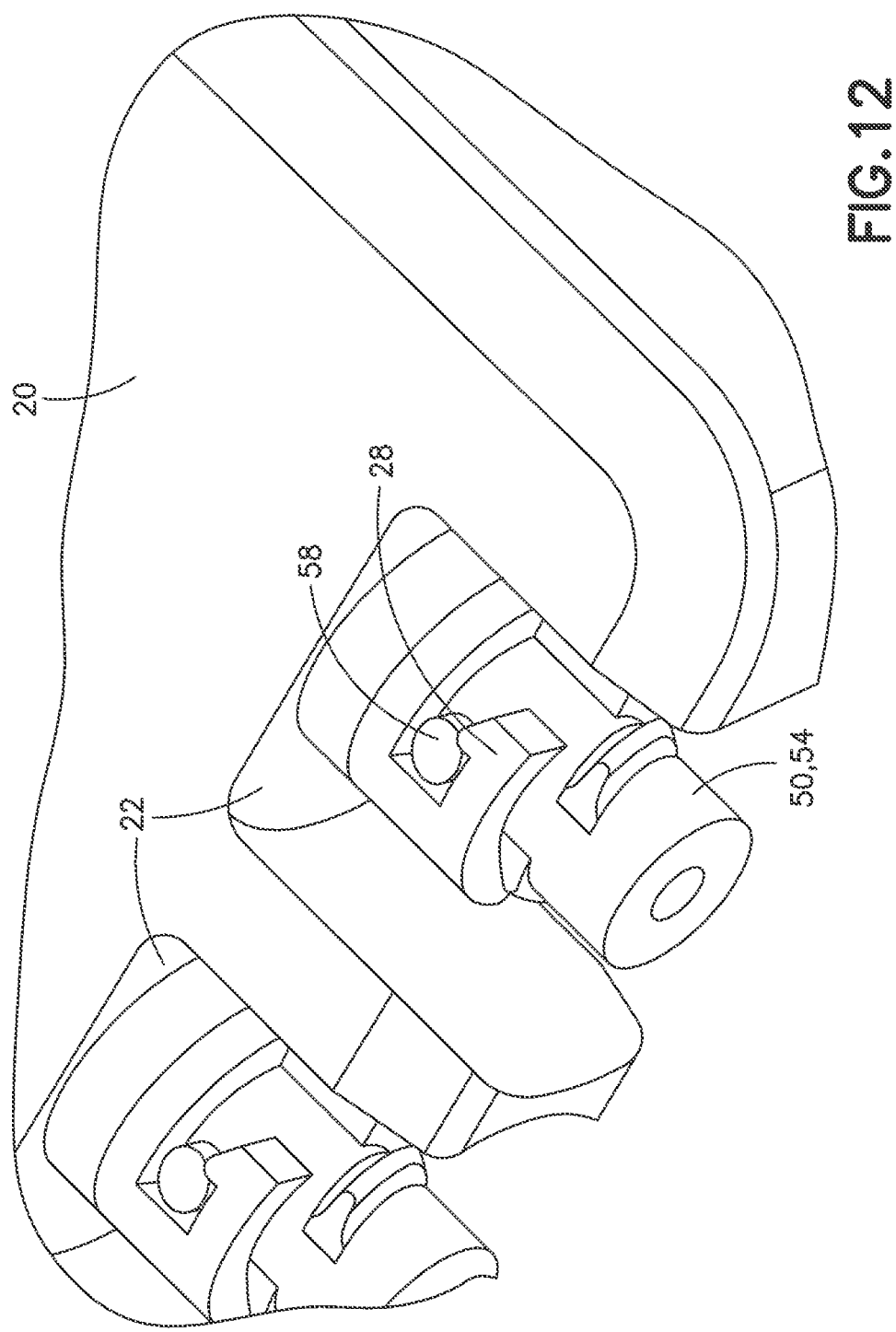
FIG. 12 illustrates a right perspective view of the needle hub in the magazine housing in a locked position.

FIG. 10 illustrates, according to one embodiment, that after the selected needle hub 52 is used for medication delivery by the medication pen 2, the medication pen 2 returns the selected needle hub 52 back to the magazine housing 20. Specifically, the selected needle hub 52 engages the connector 28 in the selected hub chamber 24 of the magazine housing 20. The selected needle hub 52 returns to the selected hub chamber 24 that it was originally sealed in. FIGS. 11 and 12 illustrate the operation of the connector 28 being a quarter turn bayonet connection engaging one of the plurality of needle hubs 50. Operation of the connector 28 is described below.

Figure 13:
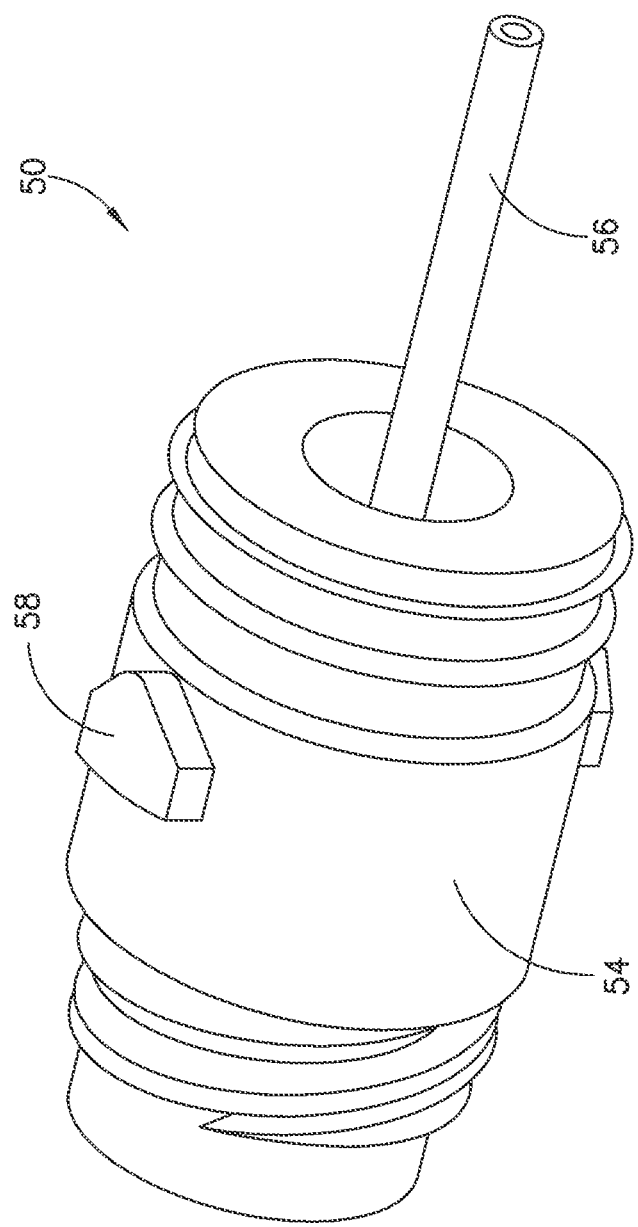
FIG. 13 illustrates a left perspective view of the needle hub.

FIG. 13 illustrates, according to one embodiment, one of the plurality of needle hubs 50. The plurality of needles hubs 50 is preferably made of an infrared reflective material and each of the plurality of needle hubs 50 includes a hub body 54, a hub cannula 56 and a radial lug 58. A proximal and distal end of the hub body 54 preferably includes threads or the push-pull detent. The proximal end of the hub body 54 is configured to be attached to the adapter 4 and the distal end of the hub body 54 is configured to be attached to the connector 28 in the magazine housing 20.

The hub cannula 56 is fixed to the hub body 54 and extends from the distal end of the hub body 54. The hub cannula 56 provides a means to deliver medicament to the patient. Specifically, when one of the plurality of needle hubs 50 is connected to the medication pen 2, fluid communication is established. Accordingly, medicament travels to the needle hub 50 and exits through the hub cannula 56. Although not illustrated, the distal end of the hub cannula 56 includes a sharpened bevel cut that is configured to penetrate tissue.

The radial lug 58 is disposed adjacent to the threads or the push-pull detent at the distal end of the hub body 54. The radial lug 58 acts as a secondary retention means to the connector 28 in the magazine housing 20. Two radial lugs 58 are preferably disposed on the hub body 54 approximately 180° apart.

As illustrated in FIG. 11, when the used needle hub 50 is returned to the magazine housing 20, the used needle hub 50 engages the quarter turn connector 28 via the radial lug 58. The used needle hub 50 is then rotated approximately 90°, as illustrated in FIG. 12, to engage the quarter turn connector 28 of the magazine housing 20. Thus, the quarter turn connector 28 is secured to the needle hub 52 via the radial lug 58.

Figure 14:
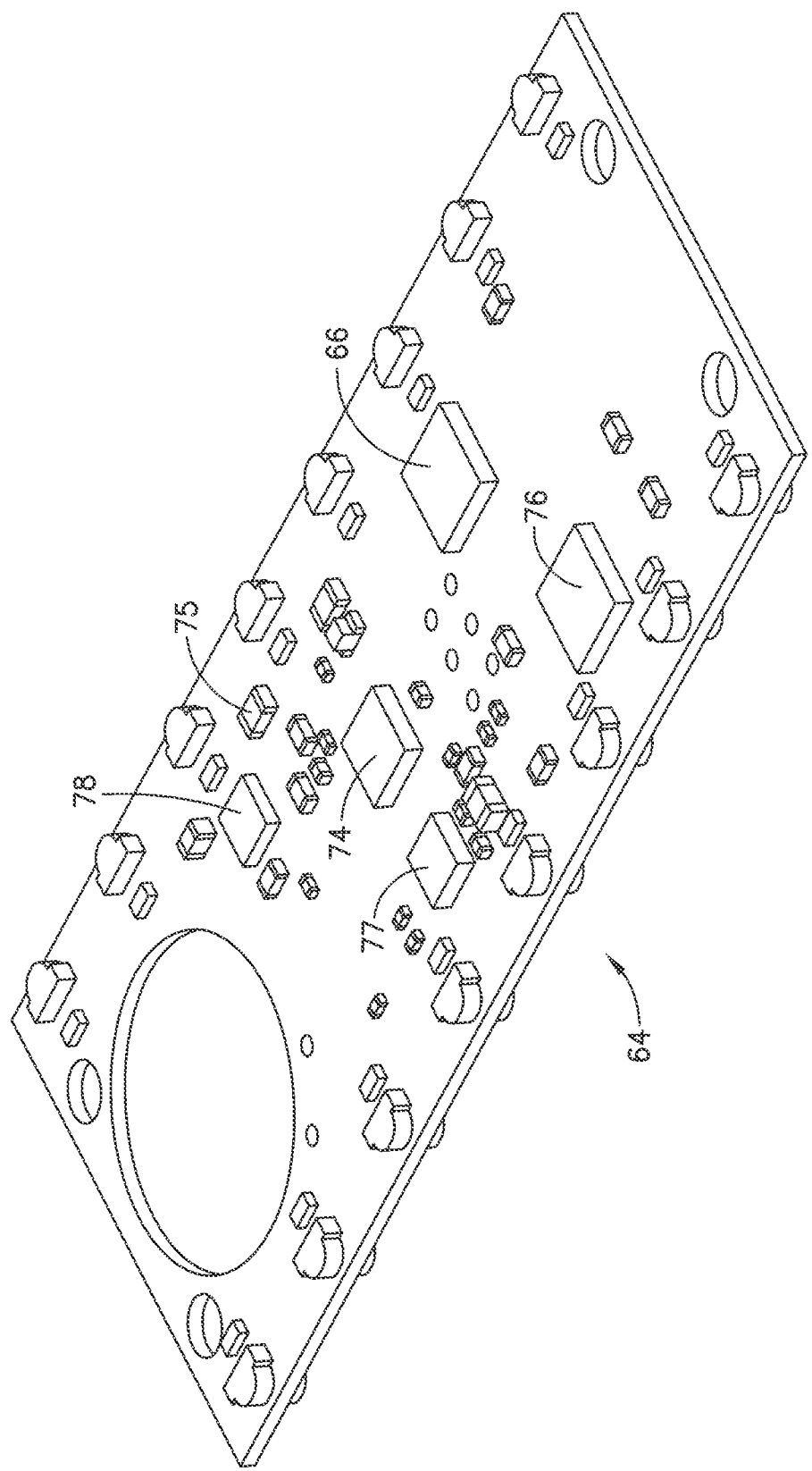
FIG. 14 illustrates a let perspective view of a printed circuit board in the magazine housing.

According to one embodiment, the magazine housing 20 includes a printed circuit board 64. The printed circuit board 64, as illustrated in FIG. 14, allows various electronic components in the magazine 18 to be disposed and to operate. For example, the printed circuit board 64 includes an inertial measurement unit 66, a battery 74, a controller 76, a memory chip 77 and a wireless module 78.

The inertial measurement unit 66 detects any vibration experienced by the magazine 18. The inertial measurement unit 66 is preferably an accelerometer but can also include, for example, a gyroscope. The inertial measurement unit 66 is calibrated to initiate operation of the magazine 18 by waking up the controller 76 on the printed circuit board 64 from a sleep state and activate its peripherals when a detected vibration, rotational movement or other gesture movement exceeds a threshold amount. The battery is always on and connected.

When the magazine 18 is not in use, the controller 76 operates in a low power sleep mode and is awakened only when triggered by the inertial measurement unit 66. In this manner, the magazine 18 is not under continuous high power use, but only when the magazine 18 is handled by a user in preparing to load a needle hub 50. Accordingly, the inertial measurement unit 66 advantageously optimizes the electrical power consumption of the magazine 18.

Alternately, the inertial measurement unit 66 is configured to detect vibration, rotational movement or other gesture movement generated by snapping the used needle hub 50 onto the connector 28 of the magazine array 26 when the used needle hub 50 is returned to the magazine housing 20. The inertial measurement unit 66 can also be configured to detect vibration, rotational movement or other gesture movement generated by, the adapter 4 snapping onto the needle hub 50 prior to removing the needle hub 50 from the connector 28 of the magazine array 26 for medication delivery. In any case, vibration exceeding the threshold amount causes the inertial measurement unit 66 to alert the controller 76 and check the status of the needle hubs 50 via the infrared reflective system 68.

The printed circuit board 64 further includes the battery 74 that regulates and provides a steady voltage source of electrical power to operate the electrical components of the magazine housing 20. Preferably, the battery 74 is a coin cell battery that is optimally sized and sufficiently powered.

The controller 76 is also disposed on the printed circuit board 64. The controller 76 provides the following functional benefits. The controller 76 receives time and data, as well as any other user information via the wireless module 78 such as a Bluetooth transmitter. Specifically, the controller 76 measures time through a global positioning system (GPS) or alternatively includes a real time clock 75 (e.g., Abracon AB-RTCMC real-time clock module or equivalent thereof). The real time clock 75 maintains accurate time and stores time corresponding to the logging data in the memory chip 77.

As described below, the controller 76 cooperates with the infrared reflective system 68 to determine the status of each of the plurality of needle hubs 50. This occurs when a magazine array 26 is installed in the magazine housing 20 and at any point during operation of the magazine 18. Subsequently, the controller 76 communicates with the electronic indicator 62 to display the status of the plurality of needle hubs 50 to the user. Specifically, the controller 76 activates the appropriate LEDs 80 in the color defined manner described above. The controller 76 also transfers the data regarding the status of the plurality of needle hubs 50 in real-time. This transfer occurs via the wireless module 78 such as Wi-Fi technology or the Bluetooth transmitter as described below.

The memory chip 77 is also disposed on the printed circuit board 64. The memory chip 77 is a non-volatile memory storage medium that stores data from the infrared reflective system 68 and the controller 76. The controller 76 transfers data to and from the memory chip 77, as well as to the wireless module 78 for data communication. The controller 76 also stores processed data on the memory chip 77.

The wireless module 78 is also disposed on the printed circuit board 64. The wireless module 78 provides data communication between the magazine 18 and an external system such as a smart phone or a computer. Alternatively, Wi-Fi technology can be used in place of the wireless module 78 for similar purposes.

In an alternate configuration, a controller and a memory chip included in a standard Bluetooth chip may be sufficient and not require these components separately on the printed circuit board 64. In this instance, the Bluetooth chip will require various simple circuit elements such as resistors, capacitors and diodes to function properly.

Figure 14A:
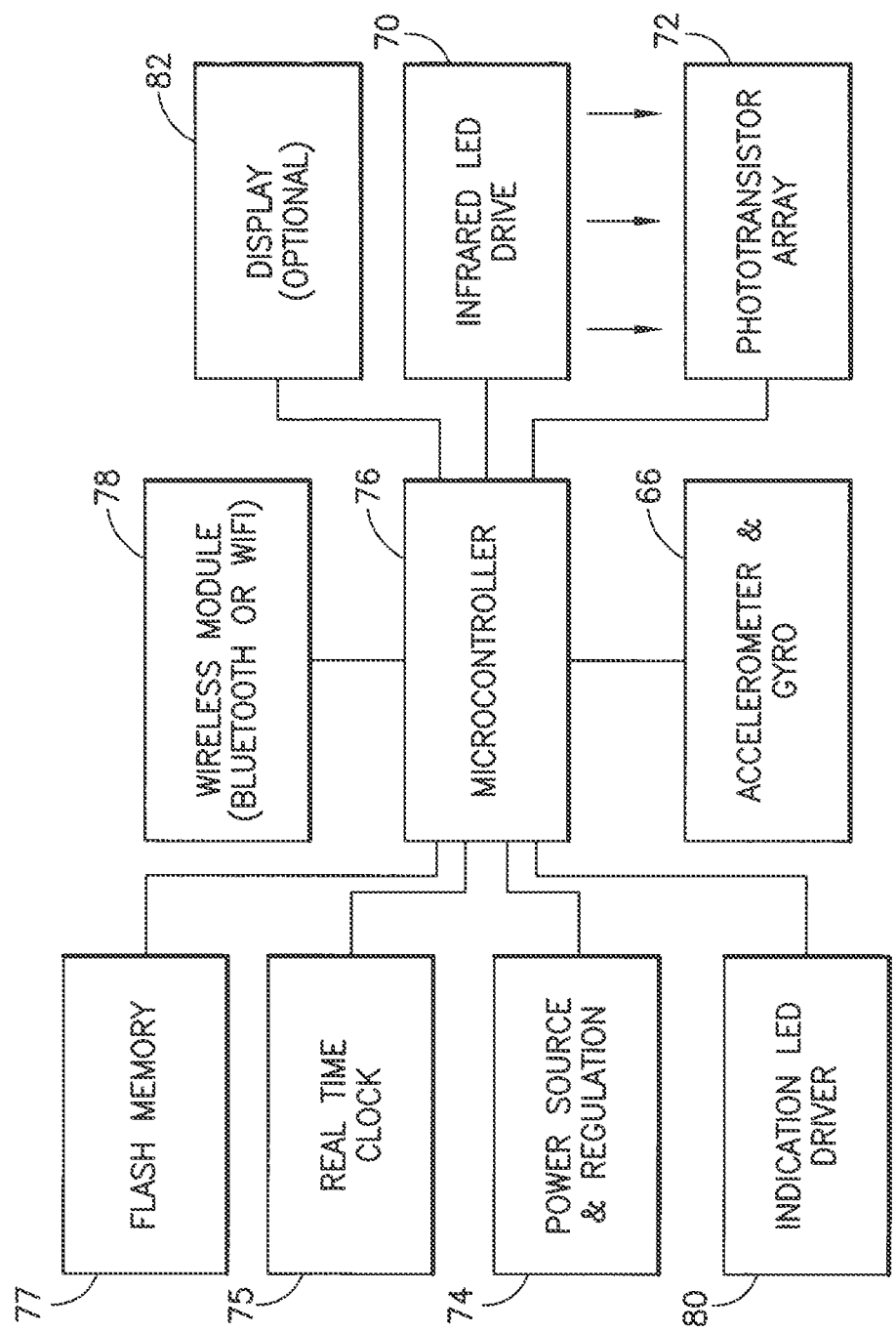
FIG. 14A illustrates a block diagram of the operation of the printed circuit board in the magazine housing.

FIG. 14A illustrates a block diagram showing the operation of the printed circuit board 64 in the magazine 18. Specifically, the memory chip 77, the clock 75, the battery 74 and the LEDs 80 cooperate with the controller 76 for appropriate operation as described above. The controller 76 also communicates with the inertial measurement unit 66 and the wireless module 78 for efficient power usage and transfer of data.

The block diagram of FIG. 14A also illustrates the controller 76 communicating with an electronic display 82, an array of infrared emitters 70 and an array of infrared detectors 72. Operation of these features is further described below.

Figure 15:
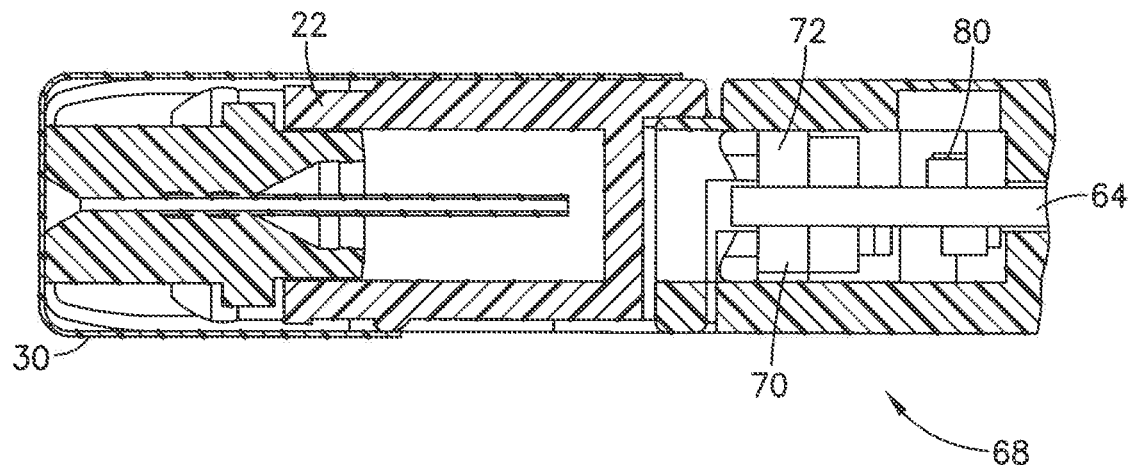
FIG. 15 illustrates a partial cross sectional view of a removable magazine array connected to the magazine housing including an infrared reflective system.
Figure 16:
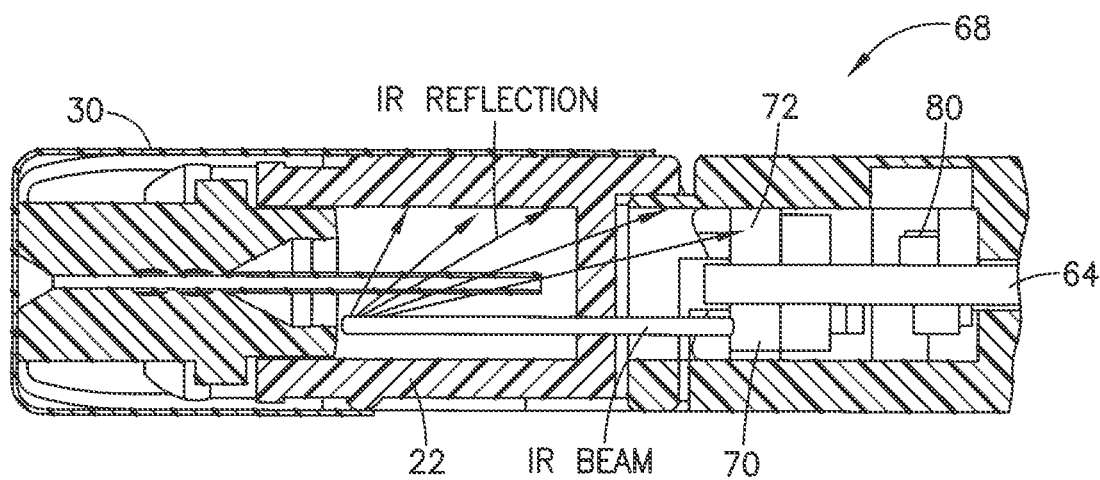
FIG. 16 illustrates the partial cross sectional view of the removable magazine assembly connected to the magazine housing of FIG. 15 with the infrared reflective system detecting an unused needle hub.
Figure 17:
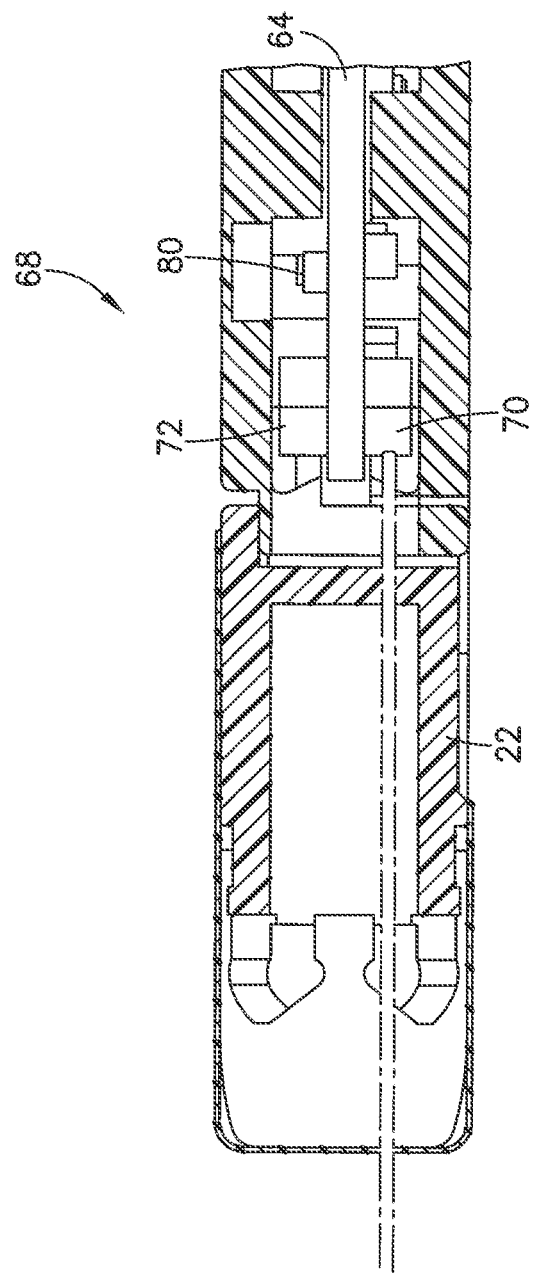
FIG. 17 illustrates the partial cross sectional view of the removable magazine assembly connected to the magazine housing of FIG. 15 with the infrared reflective system detecting an empty hub chamber.

According to one embodiment, the magazine 18 further includes the infrared reflective system 68. FIGS. 15-17 illustrate the infrared reflective system 68 including the array of infrared emitters 70 and the array of infrared detectors 72. The array of infrared emitters 70 is a plurality of infrared emitters 70 each assigned to a respective hub chamber 22 of the plurality of hub chambers 22.

The infrared emitters 70, also referred to as infrared LED drivers, are disposed in the magazine housing 20 and emit or radiate infrared light into an opening in the magazine housing 20 (or through a wall of the magazine housing 20) and into a hub chamber 22. In other words, the infrared emitters 70 beams infrared light into a magazine bay of the magazine housing 20.

Similarly, the array of infrared detectors 72, also referred as a phototransistor array, is a plurality of infrared detectors 72 each assigned to a respective hub chamber 22 of the plurality of hub chambers 22. The infrared detectors 72 are disposed in the magazine housing 20 and receive or detect reflected infrared light. In other words, the infrared detectors 72 rod in reflected infrared right within the magazine bay of the magazine housing 20.

As described above, the magazine housing 20 is composed of an infrared translucent material and the plurality of needle hubs 50 are composed of an infrared reflective material. The plurality of peel tabs 30 are also composed of an infrared reflective material. Alternately, these components have corresponding infrared reflective or infrared translucent coatings. This configuration allows the infrared light to travel through the magazine housing 20 and reflects when incident to the front face of the needle hubs 50 or incident to the peel tabs 30. In this manner, the presence of the needle hubs 50 is detected in the hub chambers 22. The infrared detectors 72 are connected to the printed circuit board 64 so that signals from the infrared detectors 72 are processed by the controller 76 and communicated to the memory chip 77, the wireless module 78 and/or the electronic indicator 62.

The infrared reflection system 68 operates as follows. As illustrated in FIGS. 16 and 17, each of the infrared emitters 70 radiate infrared light toward each of the hub chambers 22. Each of the infrared detectors 72 preferably detect three conditions in the plurality of hub chambers 22: (1) the hub chamber 22 is sealed by the peel tab 30 and needle hub 50 is unused and available for use; (2) the hub chamber 22 is empty, indicating that the needle hub 50 is being used; and (3) the hub chamber 22 retains the needle hub 50 but the hub chamber 22 is not sealed, indicating that the needle hub 50 is used.

Preferably, as illustrated in FIG. 16, if the needle hub 50 is present in the hub chamber 22 and the peel tab 30 seals the hub chamber 22 (condition 1), a maximum amount of infrared light is incident on the front face of the needle hub 50 and reflected back to the infrared detector 72. This is because the hub chamber 22 contains the needle hub 50 and is sealed by the peel tab 30. Moreover, the needle hub 50 and the peel tab 30 are made of an infrared reflective material to reflect the light back to the infrared detectors 72. Condition 1 is indicated by an LED 80 illuminated green.

As illustrated in FIG. 17, lithe hub chamber 22 is empty because the needle hub 50 is removed from the magazine housing 20 and the peel tab 30 is removed (condition 2), most of the infrared light exits the hub chamber 22 and is not reflected back to the infrared detectors 72. There is little infrared reflective material in the hub chamber 22 to cause the infrared light to reflect back to the infrared detectors 72. Condition 2 is indicated by an LED 80 illuminated orange.

If the needle hub 50 is present in the hub chamber 22 but the peel tab 30 is removed from the hub chamber 22 (condition 3), a nominal amount of infrared light will be reflected back to the infrared detectors 72. This is because some of the infrared light will travel through the hub cannula 56 of the needle hub 50 and exit the hub chamber 22 since the peel tab 30 is removed. On the other hand, some of the infrared light will be incident to the front face of the needle hub 50 and reflect back to the infrared detectors 72. Condition 3 is indicated by an LED 80 illuminated red.

The infrared detectors 72 are calibrated to detect the three different reflected infrared luminance ranges corresponding to each of the conditions described above. A new needle hub 50 sealed in a hub chamber 22 provides the greatest reflected infrared light. A used hub 50 not being sealed in a hub chamber 22 provides less reflected infrared light than a new needle hub 50. An empty hub chamber 22 provides the least reflected light of all the three conditions.

Due to changing ambient lighting conditions, an algorithm can be used to remove a lighting offset from the infrared detector 72 data to provide more accurate readings. Each needle hub 50 is measured with and without the infrared emitter 70 powered on to provide a differential measurement created between ambient and emitter lit conditions. A plurality of measurements is made for each hub chamber 22 to average out any noise in measurement. Finally, the hub chambers 22 are compared against each other and against dynamic infrared sensing thresholds.

The controller 76 then receives the signals from the array of infrared detectors 72 and communicates appropriate signals to the electronic indicator 62. As illustrated in FIG. 18, the LED 80 of one of the plurality of hub chambers 22 is red indicating that the needle hub 50 is used (condition 3). The remaining LEDs 80 corresponding to the remaining hub chambers 22 are green indicating that the hub chamber 22 is sealed by the peel tab 30 and the needle hub 50 is unused (condition 1).

Figure 19:
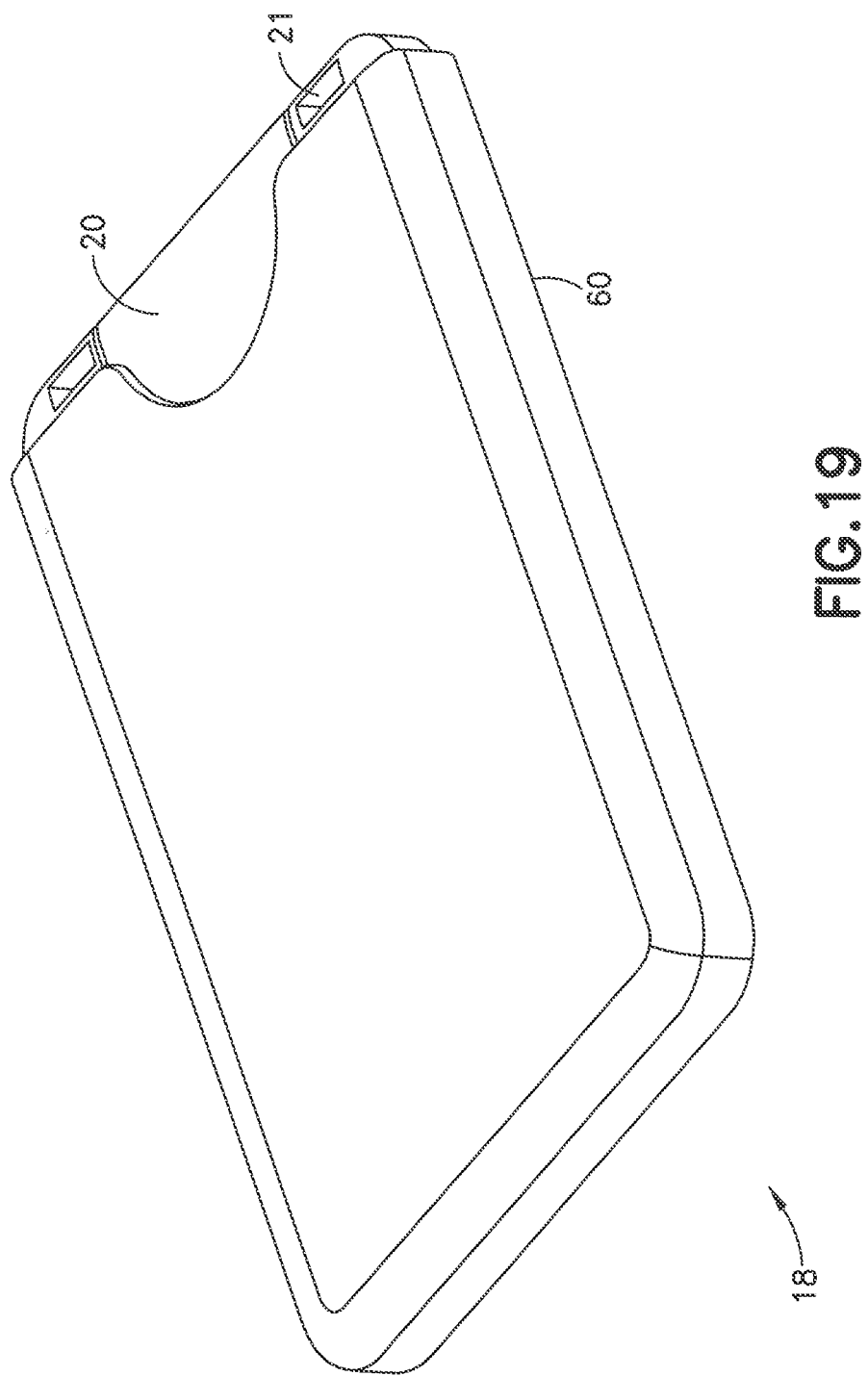
FIG. 19 illustrates another embodiment of the magazine enclosed by a cover.

According to another embodiment, the magazine 18 includes a cover 60 and an electronic indicator 62 being an electronic display 52. FIG. 19 illustrates the magazine 18 including the cover 60 that encloses the magazine housing 20. The cover 60 protects the needle hubs 50 in the magazine 18 from inadvertent use.

Figure 20:
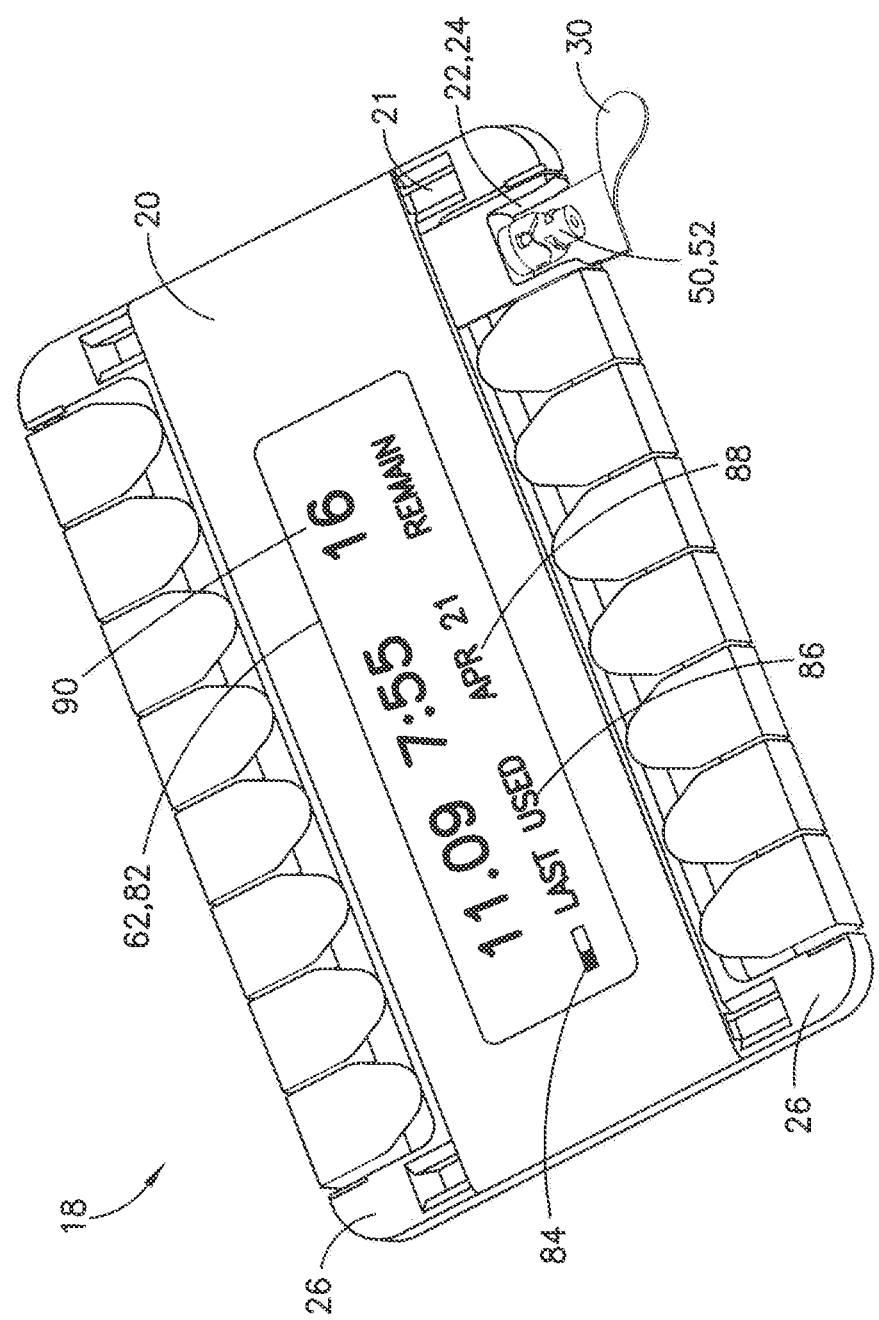
FIG. 20 illustrates the magazine of FIG. 19 with the cover removed and including a display.
Figure 21:
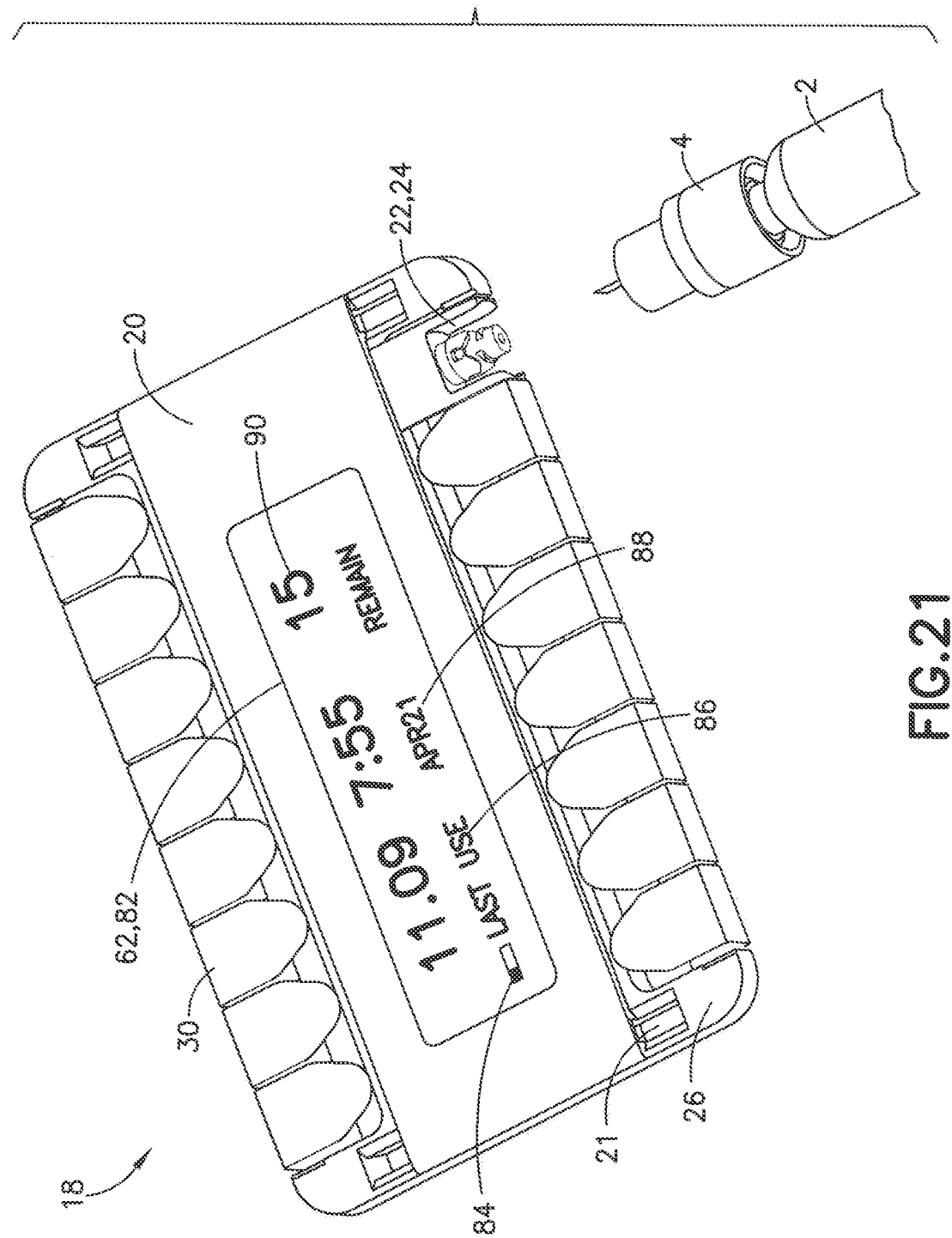
FIG. 21 illustrates the magazine of FIG. 20 with a needle hub removed from the magazine housing.
Figure 22:
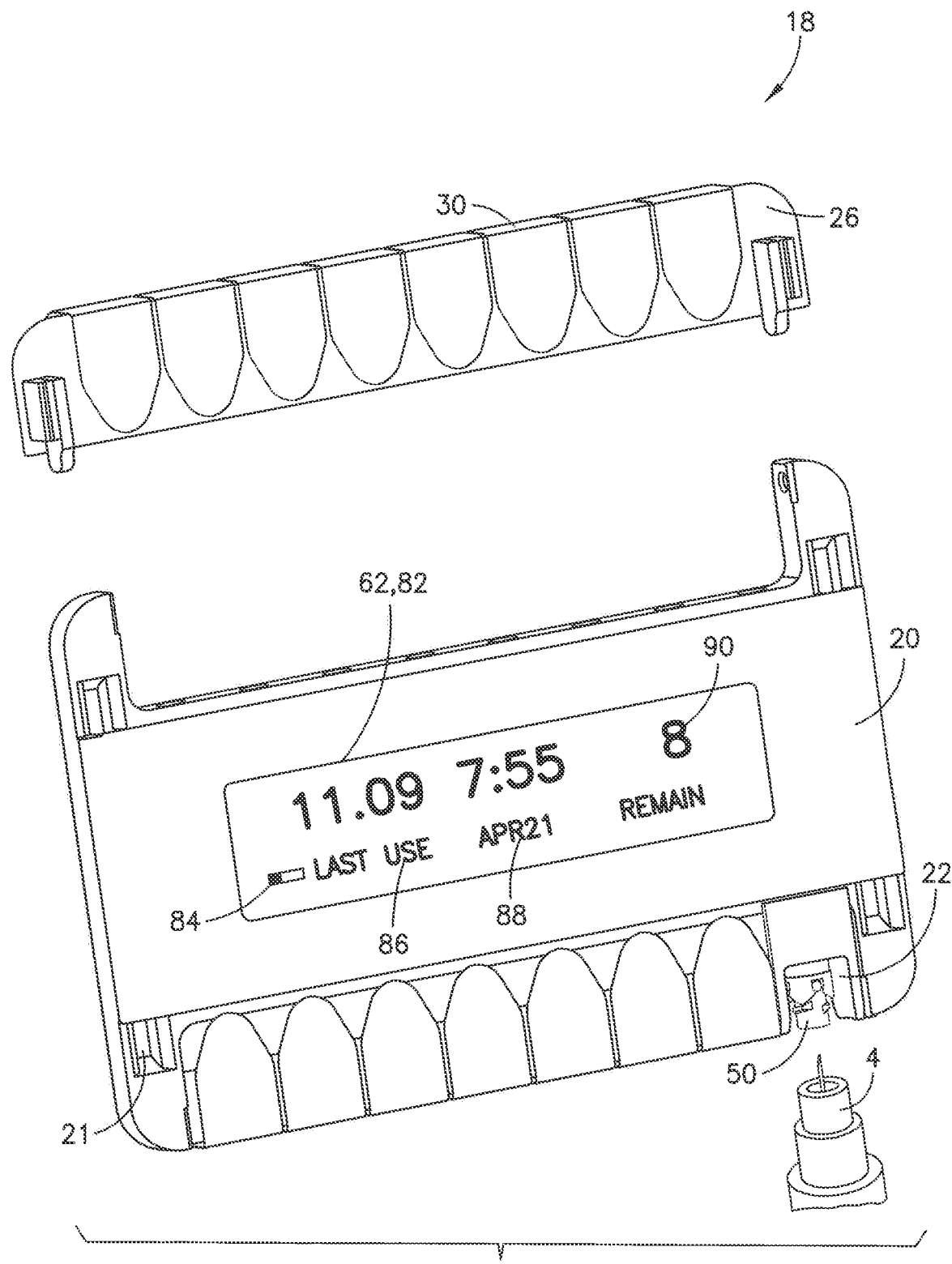
FIG. 22 illustrates the magazine of FIG. 20 with the used needle hub returned to the magazine housing and the removable magazine array disengaging the magazine housing.

FIGS. 20-22 illustrate the electronic indicator 62 being an electronic display 82. The electronic display 82 is preferably an LCD display or alternatively an E-ink display. The electronic display 82 presents information to the user that describes the state of the magazine 18. For example, the electronic display 82 shows a battery level 84, a use status 86 indicating when the last needle hub 50 was removed from the magazine housing 20, current conditions 88 indicating a date and a time, and a number of present needle hubs 90. Based on the use of the needle hub 50, the controller 76 also determines the projected replacement time of the magazine 18 or of the magazine array 26. The electronic display 82 communicates with the controller 76, the memory chip 77 and the infrared reflective system 68 as described above to determine and display these characteristics of the magazine 18.

Specifically, the battery level 84 displays how much electrical power is remaining in the battery 74 to operate the magazine 18. The use status 86 displays a day and month of when the last needle hub 50 was removed from the magazine housing 20. The current conditions 88 display a date and time in real-time. Finally, the number of present needle hubs 90 displays a number of the plurality of needle hubs 50 that are in the magazine array 26. Alternately, the number of present needle hubs 90 can display the number of unused needle hubs 50.

FIG. 20 illustrates the peel tab 30 being removed from the selected hub chamber 24 to expose the selected needle hub 52 for use. FIG. 21 illustrates the medication pen 2 connected to the adapter 4 that engages the selected needle hub 52 and removes the selected needle hub 52 from the selected hub chamber 24 in the magazine array 26 of the magazine housing 20. As a result, the electronic display 82 indicating the number of present needle hubs 90 is reduced from 16 to 15.

FIG. 22 illustrates the used needle hub 50 returned to the magazine array 26 of the magazine housing 20. Thus, one of the magazine arrays 26 includes the used needle hub 50 and seven unused needle hubs 50. The other magazine array 26 is removed from the magazine housing 20. As a result, the electronic display 82 indicating the number of needle hubs present 90 is reduced from 16 to 8. The electronic display 82 advantageously provides important information about the needle hubs 50 for the user to optimize the use of the magazine 18 and prevent reuse of the needle hubs 50. Additionally, the magazine housing 20 is advantageously reusable by replacing the magazine arrays 26 when all the needle hubs 50 are used.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplar); embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. A magazine that stores a plurality of needles configured to engage a medication pen for medication delivery, the magazine comprising:
    a magazine housing including one of mounting recesses and mounting projections, the magazine housing enclosing:
        a removable array including the other of the mounting recesses and mounting projections, and having a plurality of hub chambers each enclosing one of a plurality of needle hubs, the mounting projections engaging the mounting recesses to secure the removable array to the magazine housing;
        a connector in each of the plurality of hub chambers, each connector engaging one of the plurality of needle hubs;
        a plurality of closures each sealing one of the plurality of hub chambers; and
        an electronic indicator to identify a status of the plurality of needle hubs, wherein
    the electronic indicator identifies how many of the plurality of needle hubs are unused.

2. The magazine of claim 1, wherein the removable array is replaced when the plurality of needle hubs in the removable array is all used.

3. The magazine of claim 1, wherein the removable array includes two removable arrays which are disposed opposite each other.

4. The magazine of claim 1, wherein the electronic indicator includes a plurality of LEDs.

5. The magazine of claim 1, wherein the magazine housing includes a circuit board.

6. The magazine of claim 1, wherein the electronic indicator includes an infrared reflective system that emits infrared light to determine the status of the plurality of needle hubs.

7. The magazine of claim 1, wherein
    the magazine housing comprises an infrared translucent material; and
    the plurality of needle hubs comprises an infrared reflective material.

8. The magazine of claim 1, wherein the removable array is linearly arranged.

9. The magazine of claim 1, wherein each hub in the removable array is simultaneously accessible to a user.

10. The magazine of claim 1, wherein the plurality of hub chambers in the removable array is positionally fixed in the magazine housing during operation.

11. The magazine of claim 1, wherein the electronic indicator includes an electronic display.

12. The magazine of claim 11, wherein the electronic display includes at least one of a battery level, use status, current conditions and a number of the unused needle hubs.

13. The magazine of claim 12, wherein the current conditions display the current date and time.

14. The magazine of claim 12, wherein the use status displays a time when a most recent needle hub of the plurality of needle hubs was removed from the magazine housing.

15. A method of using a plurality of needles in a magazine, the plurality of needles configured to engage a medication pen for medication delivery, the method comprising:
    removing a selected closure of a plurality of closures to expose a selected needle hub of a plurality of needle hubs in a removable array of a magazine housing;
    engaging the medication pen to the selected needle hub;
    disengaging the selected needle hub from the magazine housing to prepare the medication pen for medication delivery;
    indicating a status of the plurality of needles by identifying how many of the plurality of needle hubs are unused; and
    disengaging mounting projections from mounting recesses to remove the removable array from the magazine and replace the removable array after all of the plurality of needles are used.

16. A magazine that stores a plurality of needles configured to engage a medication pen for medication delivery, the magazine comprising:
    a magazine housing enclosing:
        a removable array having a plurality of hub chambers each enclosing one of a plurality of needle hubs;
        a connector in each of the plurality of hub chambers, each connector engaging one of the plurality of needle hubs;
        a plurality of closures each sealing one of the plurality of hub chambers; and
        an electronic indicator to identify a status of the plurality of needle hubs, wherein
    the electronic indicator includes a plurality of LEDs that identifies how many of the plurality of needle hubs are unused; wherein
    each of the plurality of LEDs is aligned to one of the plurality of hub chambers.

17. A magazine that stores a plurality of needles configured to engage a medication pen for medication delivery, the magazine comprising:
    a magazine housing enclosing:

a removable array having a plurality of hub chambers each enclosing one of a plurality of needle hubs;

a connector in each of the plurality of hub chambers, each connector engaging one of the plurality of needle hubs;

a plurality of closures each sealing one of the plurality of hub chambers; and an electronic indicator to identify a status of the plurality of needle hubs, wherein the electronic indicator includes a plurality of LEDs that identifies how many of the plurality of needle hubs are unused; wherein when one of the plurality of LEDs corresponding to one of the plurality of hub chambers illuminates in a selected color, the corresponding needle hub of the plurality of needle hubs is used.

18. A magazine that stores a plurality of needles configured to engage a medication pen for medication delivery, the magazine comprising:

a magazine housing enclosing:

a removable array having a plurality of hub chambers each enclosing one of a plurality of needle hubs;

a connector in each of the plurality of hub chambers, each connector engaging one of the plurality of needle hubs;

a plurality of closures each sealing one of the plurality of hub chambers; and an electronic indicator to identify a status of the plurality of needle hubs, wherein the electronic indicator includes a plurality of LEDs that identifies how many of the plurality of needle hubs are unused; and when one of the plurality of LEDs corresponding to one of the plurality of hub chambers illuminates in a selected color, the corresponding needle hub of the plurality of needle hubs is new and available for use.

19. A magazine that stores a plurality of needles configured to engage a medication pen for medication delivery, the magazine comprising:

a magazine housing enclosing:

a removable array having a plurality of hub chambers each enclosing one of a plurality of needle hubs;

a connector in each of the plurality of hub chambers, each connector engaging one of the plurality of needle hubs;

a plurality of closures each sealing one of the plurality of hub chambers; and an electronic indicator to identify a status of the plurality of needle hubs, wherein the electronic indicator identifies how many of the plurality of needle hubs are unused; and the magazine housing includes a circuit board having an inertial measurement unit that detects vibration, the inertial measurement unit triggers operation of the circuit board when a predetermined vibration value is exceeded.

20. A magazine that stores a plurality of needles configured to engage a medication pen for medication delivery, the magazine comprising:

a magazine housing enclosing:

a removable array having a plurality of hub chambers each enclosing one of a plurality of needle hubs;

a connector in each of the plurality of hub chambers, each connector engaging one of the plurality of needle hubs;

a plurality of closures each sealing one of the plurality of hub chambers; and an electronic indicator to identify a status of the plurality of needle hubs, wherein the electronic indicator identifies how many of the plurality of needle hubs are unused;

the electronic indicator includes an infrared reflective system that emits infrared light to determine the status of the plurality of needle hubs;

the infrared reflective system includes a plurality of infrared emitters and a plurality of infrared detectors; and one of the plurality of infrared emitters and one of a plurality of infrared detectors are aligned to each other in each one of the plurality of hub chambers.

21. A magazine that stores a plurality of needles configured to engage a medication pen for medication delivery, the magazine comprising:

a magazine housing enclosing:

a removable array having a plurality of hub chambers each enclosing one of a plurality of needle hubs;

a connector in each of the plurality of hub chambers, each connector engaging one of the plurality of needle hubs;

a plurality of closures each sealing one of the plurality of hub chambers; and an electronic indicator to identify a status of the plurality of needle hubs, wherein the electronic indicator identifies how many of the plurality of needle hubs are unused;

the electronic indicator includes an infrared reflective system that emits infrared light to determine the status of the plurality of needle hubs; and based on infrared light reflection received, the infrared reflective system identifies one of an empty hub chamber, an unused needle hub in the hub chamber and a used needle hub in the hub chamber.

* * * * *